United States Patent
Kataoka

(10) Patent No.: US 11,201,352 B2
(45) Date of Patent: Dec. 14, 2021

(54) ELECTROLYTIC SOLUTION FOR NON-AQUEOUS SECONDARY BATTERY, NON-AQUEOUS SECONDARY BATTERY, AND METAL COMPLEX

(71) Applicant: FUJIFILM Corporation, Tokyo (JP)

(72) Inventor: Shohei Kataoka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 115 days.

(21) Appl. No.: 16/424,494

(22) Filed: May 29, 2019

(65) Prior Publication Data

US 2019/0280335 A1 Sep. 12, 2019

Related U.S. Application Data

(63) Continuation of application No. PCT/JP2018/000597, filed on Jan. 12, 2018.

(30) Foreign Application Priority Data

Jan. 20, 2017 (JP) .............................. JP2017-008366

(51) Int. Cl.
*H01M 10/0567* (2010.01)
*H01M 10/0569* (2010.01)
(Continued)

(52) U.S. Cl.
CPC ......... *H01M 10/0567* (2013.01); *C07C 49/14* (2013.01); *C07C 251/24* (2013.01);
(Continued)

(58) Field of Classification Search
CPC combination set(s) only.
See application file for complete search history.

(56) References Cited

U.S. PATENT DOCUMENTS 6,210,814 B1 4/2001 Thompson et al.
6,287,712 B1 9/2001 Bulovic et al.
(Continued)

FOREIGN PATENT DOCUMENTS

CN 101090903 12/2007
CN 102324564 1/2012
(Continued)

OTHER PUBLICATIONS

El-Shahawi, (Spectroelectrochemistry of Nickel(II) Complexes of N,N'-Bis(salicylaldehyde)-o-Phenylenediamine and N,N-Bis(2-hydroxy-1-naphthaldehyde)-o-Phenylenediamine), Analyst, Feb. 1994, vol. 119 (Year: 1994).*

(Continued)

*Primary Examiner* — Amanda J Barrow
(74) *Attorney, Agent, or Firm* — JCIPRNET

(57) ABSTRACT

Provided are an electrolytic solution for a non-aqueous secondary battery containing an electrolyte, an organic solvent, and a metal complex represented by General Formula (I), a non-aqueous secondary battery in which the electrolytic solution for a non-aqueous secondary battery is used, and a metal complex.

General Formula (I)

(Continued)

In General Formula (I), M represents a transition metal.
  k represents an integer of 0 or more, m represents an integer of 0 to 4, and n represents an integer of 1 or more. Here, k+n represents a valence of M.
  $R^1$ represents an alkyl group, an aryl group, an alkoxy group, a carbonyl group-containing group, a sulfonyl group-containing group, or a halogen atom.
  $R^2$ and $R^3$ represent a hydrogen atom, an alkyl group, an aryl group, an alkoxy group, a carbonyl group-containing group, a sulfonyl group-containing group, or a halogen atom.
  L represents a monodentate ligand.

5 Claims, 2 Drawing Sheets

(51) Int. Cl.
    *H01M 10/0525* (2010.01)
    *C07F 7/00* (2006.01)
    *C07C 49/14* (2006.01)
    *C07D 215/30* (2006.01)
    *C07F 7/28* (2006.01)
    *C07C 251/24* (2006.01)

(52) U.S. Cl.
    CPC .............. *C07D 215/30* (2013.01); *C07F 7/00* (2013.01); *C07F 7/003* (2013.01); *C07F 7/28* (2013.01); *H01M 10/0525* (2013.01); *H01M 10/0569* (2013.01); *H01M 2300/0025* (2013.01)

(56) References Cited

U.S. PATENT DOCUMENTS

| | | |
|---|---|---|
| 6,312,836 B1 | 11/2001 | Bulovic et al. |
| 7,230,107 B1 | 6/2007 | Herron et al. |
| 7,557,233 B2 | 7/2009 | Isono et al. |
| 7,838,127 B1 | 11/2010 | Wang et al. |
| 9,735,448 B2 * | 8/2017 | Ishiji ................ H01M 10/0567 |
| 10,084,203 B2 | 9/2018 | Ishui et al. |
| 2002/0045063 A1 | 4/2002 | Kim et al. |
| 2002/0045064 A1 | 4/2002 | Kim et al. |
| 2002/0045065 A1 * | 4/2002 | Kim .................... H01L 51/0089 428/690 |
| 2002/0081496 A1 * | 6/2002 | Tsujioka ................ H01G 11/56 429/307 |
| 2007/0065719 A1 * | 3/2007 | Timonov ............... H01M 4/381 429/213 |
| 2011/0095269 A1 | 4/2011 | Zhang et al. |
| 2015/0072246 A1 | 3/2015 | Ishui et al. |
| 2015/0295276 A1 * | 10/2015 | Ishiji ................ H01M 10/0525 429/188 |
| 2017/0069936 A1 * | 3/2017 | Woo ...................... H01M 4/587 |
| 2019/0157720 A1 * | 5/2019 | Kataoka ............ H01M 10/0567 |

FOREIGN PATENT DOCUMENTS

| | | |
|---|---|---|
| CN | 104272521 | 1/2015 |
| EP | 1842853 | 10/2007 |
| EP | 1843426 | 10/2007 |
| JP | S6286673 | 4/1987 |
| JP | H11080173 | 3/1999 |
| JP | 2000053957 | 2/2000 |
| JP | 2001155//2 | 6/2001 |
| JP | 2004063432 | 2/2004 |
| JP | 2007265858 | 10/2007 |
| JP | 2013242999 | 12/2013 |
| JP | 2014146481 | 8/2014 |
| JP | 2016213101 | 12/2016 |
| KR | 20160063905 | 6/2016 |
| WO | 9953724 | 10/1999 |

OTHER PUBLICATIONS

Brecher, J. Graphical Representation Standards for Chemical Structure Diagrams (IUPAC Recommendations 2008). Pure and Applied Chemistry 2009, 80 (2), p. 393, accessed at https://doi.org/10.1351/pac200880020277 (copy provided). (Year: 2009).*
"Office Action of Japan Counterpart Application", dated Jun. 16, 2020, with English translation thereof, p. 1-p. 6.
"International Search Report (Form PCT/ISA/210) of PCT/JP2018/000597," dated Feb. 13, 2018, with English translation thereof, pp. 1-5.
"Written Opinion of the International Searching Authority (Form PCT/ISA/237) of PCT/JP2018/000597," dated Feb. 13, 2018, with English translation thereof, pp. 1-8.
"Office Action of China Counterpart Application" with English translation thereof, dated Sep. 1, 2021, p. 1-p. 12.

* cited by examiner

ELECTROLYTIC SOLUTION FOR NON-AQUEOUS SECONDARY BATTERY, NON-AQUEOUS SECONDARY BATTERY, AND METAL COMPLEX

CROSS-REFERENCE TO RELATED APPLICATIONS

This application is a Continuation of PCT International Application No. PCT/JP2018/000597 filed on Jan. 12, 2018, which claims priority under 35 U.S.C. § 119 (a) to Japanese Patent Application No. 2017-008366 filed in Japan on Jan. 20, 2017. Each of the above applications is hereby expressly incorporated by reference, in its entirety, into the present application.

BACKGROUND OF THE INVENTION

1. Field of the Invention

The present invention relates to an electrolytic solution for a non-aqueous secondary battery, a non-aqueous secondary battery, and a metal complex.

2. Description of the Related Art

Lithium ion secondary batteries are capable of realizing charging and discharging of a larger energy density compared with secondary batteries of the related art (for example, lead batteries and nickel cadmium batteries). Lithium ion secondary batteries have been broadly applied to portable electronic devices such as mobile phones and notebook computers using the above-described characteristic. Recently, in response to the extension of the applicable use, active research and development has been underway for the improvement of the battery characteristics of lithium ion secondary batteries. Particularly, in response to the development of the use in transportation devices including cars, there has been a demand for additional technical development for the additional improvement in performance regarding high-speed and large-capacity charging and discharging and safety and countermeasures to an increase in the potential of electrodes.

As one of dominant methods for improving the battery characteristics of lithium ion secondary batteries, a technique of adding an additive to an electrolytic solution has been proposed. For example, the use of a variety of additives for the purpose of improving cycle characteristic which is one of battery characteristics has been reported (refer to JP1987-086673A (JP-S62-086673A), JP2001-155772A, JP2004-063432A, JP2007-265858A, and JP2014-146481A).

SUMMARY OF THE INVENTION

Hitherto, as a functional additive added to improve the cycle characteristics, organic compounds having a low molecular weight such as benzophenone or succinic acid have been mainly studied (refer to JP1987-086673A (JP-S62-086673A), JP2001-155772A, JP2004-063432A, and JP2007-265858A). Although the action mechanism thereof has not been clarified, it is considered that the organic compounds mainly act on a negative electrode and thus bring about the effect. Meanwhile, JP2014-146481A describes an organic metal compound that acts on a positive electrode instead of a negative electrode.

Recently, non-aqueous secondary batteries that can be driven at a higher potential have been demanded. In order to realize the high-potential driving and enable non-aqueous secondary batteries to satisfy a high level of requirements regarding battery performance such as cycle characteristics, it is necessary to suppress the oxidation and decomposition of an organic solvent or the like that is included in an electrolytic solution on the positive electrode surface during the high-potential driving. As one of means for suppressing the oxidation and decomposition, the formation of a solid electrolyte interphase (SEI) coating on the positive electrode surface at a high potential is considered to be effective.

In consideration of the above-described circumstance, an object of the present invention is to provide an electrolytic solution for a non-aqueous secondary battery capable of effectively suppressing the oxidation and decomposition of an organic solvent or the like on a positive electrode surface even during the driving of a non-aqueous secondary battery at a higher potential (for example, approximately 5 V). In addition, another object of the present invention is to provide a non-aqueous secondary battery in which the above-described electrolytic solution for a non-aqueous secondary battery is used. Furthermore, still another object of the present invention is to provide a metal complex that is preferable for the use in the above-described electrolytic solution for a non-aqueous secondary battery.

In order to develop non-aqueous secondary batteries that can be driven at a high potential, the present inventors repeated intensive studies mainly about a compound for forming a positive electrode SEI coating. As a result, it was found that, in a case in which a specific metal complex represented by General Formula (I) is added to an electrolytic solution in a non-aqueous secondary battery and the non-aqueous secondary battery is driven at a high potential, it is possible to effectively suppress the oxidation and decomposition of an organic solvent or the like that is included in the electrolytic solution. The present invention was completed on the basis of such a technique.

The above-described objects were achieved by the following means.

<1> An electrolytic solution for a non-aqueous secondary battery comprising: an electrolyte; an organic solvent; and a metal complex represented by General Formula (I).

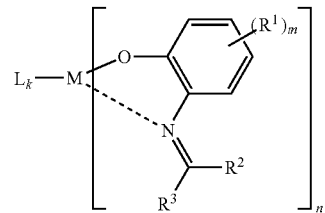

General Formula (I)

In General Formula (I), M represents a transition metal.

k represents an integer of 0 or more, m represents an integer of 0 to 4, and n represents an integer of 1 or more. Here, k+n represents a valence of M.

$R^1$ represents an alkyl group, an aryl group, an alkoxy group, a carbonyl group-containing group, a sulfonyl group-containing group, or a halogen atom.

$R^2$ and $R^3$ represent a hydrogen atom, an alkyl group, an aryl group, an alkoxy group, a carbonyl group-containing group, a sulfonyl group-containing group, or a halogen atom.

L represents a monodentate ligand.

<2> The electrolytic solution for a non-aqueous secondary battery according to <1>, in which the metal complex represented by General Formula (I) is a metal complex represented by General Formula (II).

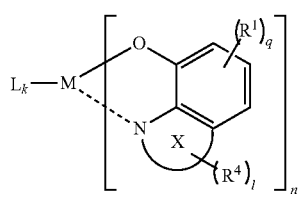

General Formula (II)

In General Formula (II), k, n, M, $R^1$, and L are identical to k, n, M, $R^1$, and L in General Formula (I) respectively.

X represents a nitrogen-containing aromatic hetero ring.

$R^4$ represents an alkyl group, an aryl group, an alkoxy group, a carbonyl group-containing group, a sulfonyl group-containing group, or a halogen atom.

q represents an integer of 0 to 3.

l represents an integer of 0 or more.

<3> The electrolytic solution for a non-aqueous secondary battery according to <1> or <2>, in which M is Ti, Zr, or Hf.

<4> The electrolytic solution for a non-aqueous secondary battery according to any one of <1> to <3>, in which a compound having a carbonate group is included as the organic solvent.

<5> The electrolytic solution for a non-aqueous secondary battery according to any one of <1> to <4>, in which a content of the metal complex represented by General Formula (I) is 0.05 to 5% by mass.

<6> A non-aqueous secondary battery comprising: a positive electrode; a negative electrode; and the electrolytic solution for a non-aqueous secondary battery according to any one of <1> to <5>.

<7> A metal complex represented by General Formula (II).

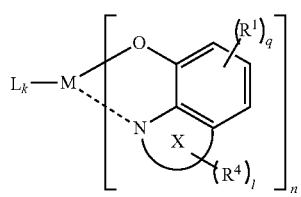

General Formula (II)

In General Formula (II), M is Ti, Zr, or Hf.

k represents an integer of 0 or more, q represents an integer of 0 to 3, l represents an integer of 0 or more, and n represents an integer of 1 or more. Here, k+n represents a valence of M.

$R^1$ represents an alkyl group, an aryl group, an alkoxy group, a carbonyl group-containing group, a sulfonyl group-containing group, or a halogen atom.

L represents a monodentate ligand.

X represents a nitrogen-containing aromatic hetero ring.

$R^4$ represents an alkyl group, an aryl group, an alkoxy group, a carbonyl group-containing group, a sulfonyl group-containing group, or a halogen atom.

In the description of the present invention, in a case in which there is a plurality of substituents, linking groups, structural units, or the like (hereinafter, referred to as substituents or the like) indicated by a specific reference or a plurality of substituents or the like is regulated simultaneously or selectively, the respective substituents or the like may be identical to or different from each other. This is also true for the regulation of the number of the substituents or the like.

In the description of the present invention, in the case of regulating the number of carbon atoms in a certain group, this number of carbon atoms refers to the number of carbon atoms in the entire group. That is, in a case in which the group further has a substituent, the number of carbon atoms refer to the number of carbon atoms not only in the group but also in the substituent.

The electrolytic solution for a non-aqueous secondary battery of an embodiment of the present invention is capable of effectively suppressing the oxidation and decomposition of an organic solvent or the like included in the electrolytic solution on a positive electrode surface even in the case of driving a non-aqueous secondary battery at a high potential by being used as an electrolytic solution for a non-aqueous secondary battery. In addition, the non-aqueous secondary battery of an embodiment of the present invention is capable of effectively suppressing the deterioration of the electrolytic solution on the positive electrode surface even at the time of being driven at a high potential. In addition, according to the present invention, it is possible to provide a metal complex capable of effectively suppressing the oxidation and decomposition of an organic solvent or the like included in the electrolytic solution on a positive electrode surface even in the case of driving a non-aqueous secondary battery at a high potential by being used in an electrolytic solution in a non-aqueous secondary battery.

DESCRIPTION OF THE PREFERRED EMBODIMENTS

[Electrolytic Solution for Non-Aqueous Secondary Battery]

Figure 1:
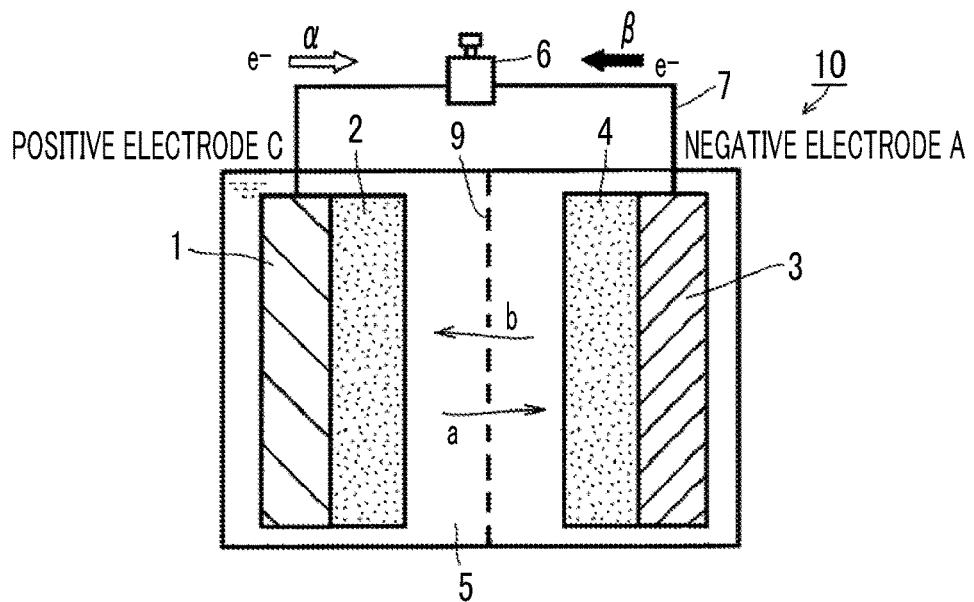
FIG. 1 is a cross-sectional view schematically showing a mechanism of a lithium ion non-aqueous secondary battery according to a preferred embodiment of the present invention.

An electrolytic solution for a non-aqueous secondary battery of an embodiment of the present invention contains an electrolyte, an organic solvent, and a metal complex represented by General Formula (I). The metal complex represented by General Formula (I) will be referred to as the metal complex (I) in some cases.

Hereinafter, a preferred embodiment of the electrolytic solution for a non-aqueous secondary battery of the embodiment of the present invention will be described.

(Electrolyte)

The electrolytic solution for a non-aqueous secondary battery of the embodiment of the present invention contains an electrolyte. As the electrolyte, a metal ion or a salt thereof is exemplified, and an ion of a metal element belonging to Group I or II of the periodic table or a salt thereof is preferred, a lithium salt, a potassium salt, a sodium salt, a calcium salt, or a magnesium salt is more preferred, and, from the viewpoint of the output of a battery, a lithium salt is particularly preferred.

In a case in which the electrolytic solution for a non-aqueous secondary battery of the embodiment of the present invention is used as an electrolytic solution for a lithium ion non-aqueous secondary battery, a lithium salt may be selected as the electrolyte. The lithium salt is not particularly limited as long as the lithium salt is a lithium salt that is ordinarily used as an electrolyte in an electrolytic solution for a lithium ion non-aqueous secondary battery, and, for example, specific examples described below can be exemplified.

Inorganic lithium salts: Inorganic fluoride salts such as $LiPF_6$, $LiBF_4$, $LiAsF_6$, and $LiSbF_6$; perhalogen acid salts such as $LiClO_4$, $LiBrO_4$, and $LiIO_4$; inorganic chloride salts such as $LiAlCL_4$; and the like.

Fluorine-containing organic lithium salts: Perfluoroalkanesulfonates such as $LiRf^1SO_3$ (for example, $LiCF_3SO_3$ and the like); perfluoroalkanesulfonylimide salts such as $LiN(Rf^1SO_2)_2$ (for example, $LiN(CF_3SO_2)_2$, $LiN(CF_3CF_2SO_2)_2$, and the like), $LiN(FSO_2)_2$, and $LiN(Rf^1SO_2)(Rf^2SO_2)$ (for example, $LiN(CF_3SO_2)(C_4F_9SO_2)$ and the like); perfluoroalkanesulfonylmethide salts such as $LiC(CF_3SO_2)_3$; perfluoroalkylfluorophosphates such as $Li[PF_5(CF_2CF_2CF_3)]$, $Li[PF_4(CF_2CF_2CF_3)_2]$, $Li[PF_3(CF_2CF_2CF_3)_3]$, $Li[PF_5(CF_2CF_2CF_2CF_3)]$, $Li[PF_4(CF_2CF_2CF_2CF_3)_2]$, and $Li[PF_3(CF_2CF_2CF_2CF_3)_3]$; and the like. Here, $Rf^1$ and $Rf^2$ each represent a perfluoroalkyl group.

Oxalate borate salts: Lithium bis(oxalate)borate, lithium difluorooxalateborate, and the like.

Among these, $LiPF_6$, $LiBF_4$, $LiAsF_6$, $LiSbF_6$, $LiClO_4$, $LiRf^1SO_3$, $LiN(Rf^1SO_2)_2$, $LiN(FSO_2)_2$, and $LiN(Rf^1SO_2)(Rf^2SO_2)$ are preferred, and $LiPF_6$, $LiBF_4$, $LiN(Rf^1SO_2)_2$, $LiN(FSO_2)_2$, and $LiN(Rf^1SO_2)(Rf^2SO_2)$ are more preferred.

Meanwhile, the lithium salt that is used in the electrolytic solution for a non-aqueous secondary battery of the embodiment of the present invention may be used singly or two or more lithium salts may be used in random combination.

The content of the electrolyte in the electrolytic solution for a non-aqueous secondary battery of the embodiment of the present invention is not particularly limited, but is preferably 10% by mass or more and 50% by mass or less and more preferably 15% by mass or more and 30% by mass or less of the total mass of the electrolytic solution for a non-aqueous secondary battery.

Meanwhile, in the case of being evaluated in terms of the concentration of an ion, the content in terms of a salt with a metal that is preferably applied may be calculated.

(Organic Solvent)

The organic solvent that is used in the electrolytic solution for a non-aqueous secondary battery of the embodiment of the present invention is not particularly limited, but is preferably an aprotic organic solvent and more preferably an aprotic organic solvent having 2 to 10 carbon atoms. The organic solvent is preferably a compound having an ether group (—O—), a carbonyl group (—C(=O)—), an ester group (—C(=O)O—), or a carbonate group (—OC(=O)O—) and more preferably a compound having a carbonate group since the compound is capable of dissolving the lithium salt that is the electrolyte in a high concentration and is relatively resistant to oxidation and reduction. Meanwhile, in the description of the present invention, the compound having an ester group (—C(=O)O—) is not classified into a compound having an ether group (—O—) or a carbonyl group (—C(=O)—), but is classified into a compound having an ester group (—C(=O)O—). Meanwhile, in the description of the present invention, the compound having a carbonate group (—OC(O)O—) is not classified into a compound having an ether group (—O—), a carbonyl group (—C(=O)—), or an ester group (—C(=O)O—), but is classified into a compound having a carbonate group (—OC(=O)O—).

These compounds may have a substituent, and specific examples of the substituent include a substituent T described below.

Examples of the organic solvent include ethylene carbonate, propylene carbonate, butylene carbonate, dimethyl carbonate, diethyl carbonate, ethyl methyl carbonate, methyl propyl carbonate, γ-butyrolactone, γ-valerolactone, 1,2-dimethoxyethane, tetrahydrofuran, 2-methyltetrahydrofuran, tetrahydropyran, 1,3-dioxolane, 4-methyl-1,3-dioxolane, 1,3-dioxane, 1,4-dioxane, methyl acetate, ethyl acetate, methyl propionate, ethyl propionate, methyl butyrate, methyl isobutyrate, trimethyl methyl acetate, ethyl trimethyl acetate, acetonitrile, glutaronitrile, adiponitrile, methoxy acetonitrile, 3-methoxypropionitrile, N,N-dimethylformamide, N-methylpyrrolidinone, N-methyloxazolidinone, N,N'-dimethylimidazolidinone, nitromethane, nitroethane, sulfolane, trimethyl phosphate, dimethyl sulfoxide, dimethyl sulfoxide phosphoric acid, vinylene carbonate (1,3-dioxole-2-one), methylvinylene carbonate (4-methyl-1,3-dioxole-2-one), ethyl vinylene carbonate (4-ethyl-1,3-dioxole-2-one), 4,5-dimethyl-1,3-dioxole-2-one, 4,5-diethyl-1,3-dioxole-2-one, 4-fluoro-1,3-dioxole-2-one, 4-trifluoromethyl-1,3-dioxole-2-one, and the like. These organic solvents may be used singly or two or more organic solvents may be jointly used. Among these, at least one of ethylene carbonate, propylene carbonate, dimethyl carbonate, diethyl carbonate, or ethyl methyl carbonate is preferred, and, particularly, a combination of a high-viscosity (high-permittivity) solvent (for example, specific permittivity ε≥30) such as ethylene carbonate or propylene carbonate and a low-viscosity solvent (for example, viscosity≤1 mPa·s) such as dimethyl carbonate, ethyl methyl carbonate, or diethyl carbonate is more preferred. This is because the dissociation property of the electrolyte salt and the mobility of the ion improve.

However, the organic solvent that is used in the present invention is not limited by the above-described exemplification.

<Compound Represented by General Formula (I)>

The electrolytic solution for a non-aqueous secondary battery of the embodiment of the present invention contains a metal complex represented by General Formula (I).

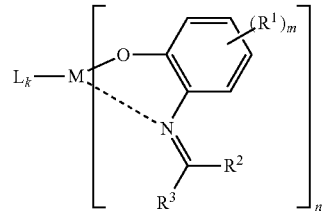

General Formula (I)

In the general formula, M represents a transition metal.

An atom of the transition metal is not particularly limited; however, for example, an iron atom (Fe), a titanium atom (Ti), a zirconium atom (Zr), a hafnium atom (Hf), and an aluminum atom (Al) are preferred, and Ti, Zr, and Hf are more preferred since oxidation and reduction derived from a change in the valence of a central metal is not easily caused up to near 5 V.

The valence of M is not particularly limited, but is preferably 2 to 6 and more preferably 3 to 5. Meanwhile, for example, the valence of Ti, Zr, and Hf is generally 4.

In the general formula, k represents an integer of 0 or more and is preferably 0 to 4 and more preferably 0 to 2.

n represents an integer of 1 or more and is preferably 1 to 4 and more preferably 2 to 4. k+n represents a valence of M. That is, k+n represents the number of atoms that covalently bond to M.

Here, in n structures indicated by [ ] in the right side of General Formula (I), a solid line that indicates the bond with M indicates a covalent bond, and a broken line that indicates the bond with M indicates a coordinate bond. A solid line that indicates the bond between L and M indicates a covalent bond and/or a coordinate bond. In a case in which the bonds between L and M are all coordinate bonds, k is zero.

Meanwhile, in a case in which the number of L's in General Formula (I) is set to t, "t+2n" represents the number of atoms that bond to M.

m represents an integer of 0 to 4 and is preferably an integer of 0 to 3, more preferably an integer of 0 to 2, and particularly preferably 0 or 1.

In the general formula, $R^1$ represents an alkyl group, an aryl group, an alkoxy group, a carbonyl group-containing group, a sulfonyl group-containing group, or a halogen atom. Meanwhile, $R^1$ may be a group obtained by combining these groups. Specifically, an alkyl-aryl group and an alkoxy-aryl group are exemplified.

The alkyl group may have a linear structure, a branched structure, or a cyclic structure and is preferably an alkyl group having 1 to 10 carbon atoms, more preferably a chain-like alkyl group having 1 to 6 carbon atoms or a cycloalkyl group having 3 to 6 carbon atoms, and particularly preferably an alkyl group having 1 to 4 carbon atoms. As the chain-like alkyl group having 1 to 6 carbon atoms, specifically, methyl, ethyl, propyl, isopropyl, butyl, t-butyl, pentyl, hexyl, and the like are exemplified, and, among these, methyl, ethyl, and t-butyl are preferred. As the cycloalkyl group having 3 to 6 carbon atoms, specifically, cyclopropyl, cyclopentyl, cyclohexyl, and the like are exemplified, and, among these, cyclohexyl is preferred.

The aryl group is preferably an aryl group having 6 to 10 carbon atoms, specifically, phenyl and naphthyl are exemplified, and, among these, phenyl is preferred.

The alkoxy group is preferably an alkoxy group having 1 to 6 carbon atoms, specifically, methoxy, ethoxy, propyloxy, isopropyloxy, cyclhexyloxy, and the like are exemplified, and, among these, methoxy and ethoxy are more preferred, and methoxy is particularly preferred.

The carbonyl group-containing group is preferably an alkoxycarbonyl group (preferably an alkoxycarbonyl group having 2 to 20 carbon atoms, for example, ethoxycarbonyl or 2-ethylhexyloxycarbonyl), a formyl group, an alkylcarbonyl group (preferably an alkylcarbonyl group having 2 to 20 carbon atoms, for example, acetyl, propionyl, or butyryl), an arylcarbonyl group (preferably an arylcarbonyl group having 6 to 20 carbon atoms, for example, benzoyl), an acyloxy group (preferably an acyloxy group having 1 to 20 carbon atoms, for example, acetyloxy or benzoyloxy), a carbamoyl group (preferably a carbamoyl group having 1 to 20 carbon atoms, for example, N,N-dimethylcarbamoyl or N-phenylcarbamoyl), or an acylamino group (preferably an acylamino group having 1 to 20 carbon atoms, for example, acetylamino or benzoylamino) and particularly preferably an alkoxycarbonyl group or an acyl group.

The sulfonyl group-containing group is preferably a sulfamoyl group-containing group (preferably a sulfamoyl group-containing group having 0 to 20 carbon atoms, for example, N,N-dimethylsulfamoyl, N-phenylsulfamoyl, sulfamoylmethyl, sulfamoylphenyl, N-methylsulfamoylmethyl, or N-ethylsulfamoylphenyl), an alkyl or arylsulfonyl group (preferably an alkyl or arylsulfonyl group having 1 to 20 carbon atoms, for example, methylsulfonyl, ethylsulfonyl, or benzenesulfonyl) and particularly preferably an alkyl or arylsulfonyl group.

The halogen atom is preferably a fluorine atom, a chlorine atom, a bromine atom, or an iodine atom and particularly preferably a fluorine atom or a chlorine atom.

In a case in which there is a plurality of $R^1$'s, the plurality of $R^1$'s may be linked together to form an aliphatic or aromatic ring (aromatic ring or aromatic hetero ring). Specific examples of the aliphatic ring include cyclopropane, cyclopentane, cyclohexane, and tetrahydropyran. Meanwhile, specific examples of the aromatic ring include benzene and naphthalene.

$R^2$ and $R^3$ represent a hydrogen atom, an alkyl group, an aryl group, an alkoxy group, a carbonyl group-containing group, a sulfonyl group-containing group, or a halogen atom. Meanwhile, $R^2$ and $R^3$ may be a group obtained by combining two or more of an alkyl group, an aryl group, an alkoxy group, a carbonyl group-containing group, a sulfonyl group-containing group, and a halogen atom. Specifically, an alkyl-aryl group and an alkoxy-aryl group are exemplified. Here, the group obtained by combining an alkyl group and an alkoxy group (alkyl-alkoxy group-) is considered as the alkoxy group.

Preferred forms of the alkyl group, the aryl group, the alkoxy group, the carbonyl group-containing group, the sulfonyl group-containing group, or the halogen atom that are represented by $R^2$ and $R^3$ are identical to the preferred forms of the alkyl group, the aryl group, the alkoxy group, the carbonyl group-containing group, the sulfonyl group-containing group, or the halogen atom exemplified as $R^1$ respectively.

$R^1$ and $R^2$ may be linked together to form an aromatic ring (aromatic ring or aromatic hetero ring). Specific examples of the aromatic ring include benzene and naphthalene.

L represents a monodentate ligand. In a case in which k is 2 or more, two L's may be linked together and have a polydentate ligand (preferably a ligand having 2 to 4 positions) form.

As L, specifically, a hydrogen atom, an alkyl group (preferably having 1 to 6 carbon atoms), an alkenyl group (preferably having 2 to 6 carbon atoms), an alkoxy group (preferably having 1 to 6 carbon atoms), an aryloxy group (preferably, an aryloxy group having 6 to 26 carbon atoms, for example, phenoxy, 1-naphthyloxy, 3-methylphenoxy, 4-methoxyphenoxy, or the like), an alkylamino group (preferably having 1 to 10 carbon atoms), a silylamino group (preferably having 0 to 10 carbon atoms), a sulfonic acid group, an isocyanato group (—NCO), an isothiocyanato group (—NCS), a sulfanyl group (R—S—) (preferably having 1 to 6 carbon atoms), a phosphinyl group ($R^aO(R^a)$PO—) (preferably having 0 to 10 carbon atoms), a carbonyl group-containing group ($R^a$—CO—) (preferably having 1 to 26 carbon atoms), a halogen atom, an aryl group (preferably having 6 to 22 carbon atoms), a heteroaryl group (preferably having 3 to 8 carbon atoms), a group obtained by combining at least two of the above-described groups, and a group obtained by linking at least two of the above-described groups using a linking group are exemplified. Here, $R^a$ represents a hydrogen atom, an alkyl group (preferably having 1 to 6 carbon atoms), or an aryl group (having 6 to 26 carbon atoms). As the linking group, —C=N—, —O—, —C(=O)—, and —C(=O)—N— are exemplified. Meanwhile, a combination of an alkyl group and an alkenyl group is considered as the alkenyl group, and a group obtained by combining an alkyl group and an alkoxy group (alkyl-alkoxy group-) is considered as the alkoxy group.

L is preferably an alkyl group, an alkenyl group, an aryl group, an aryloxy group, a carbonyl group-containing group, a group obtained by combining at least two of the above-described groups, or a group obtained by linking at least two of the above-described groups through a linking group and more preferably a methyl group, an ethenyl group, a phenyl group, a phenoxy group, a phenylcarboxy group, a methylcarboxy group, a group obtained by combining at least two of the above-described groups, or a group obtained by linking at least two of the above-described groups through a linking group. Meanwhile, the combination of an alkyl group and an alkenyl group is considered as the alkenyl group.

The metal complex (I) is preferably represented by General Formula (II).

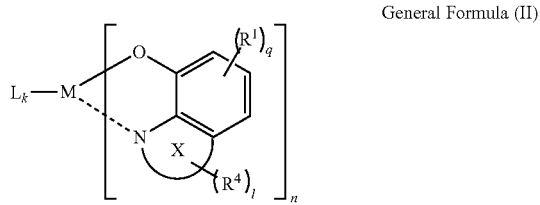

General Formula (II)

In General Formula (II), k, n, M, $R^1$, and L are identical to k, n, M, $R^1$, and L in General Formula (I) respectively.

X represents a nitrogen-containing aromatic hetero ring.

The nitrogen-containing aromatic hetero ring may include a heteroatom such as an oxygen atom or a sulfur atom in addition to a nitrogen atom in the ring structure. The nitrogen-containing aromatic hetero ring is preferably a nitrogen-containing aromatic hetero ring in which the number of carbon atoms configuring the ring is 1 to 12 (preferably a five- or six-membered ring), specifically, a pyrrole ring, a pyrazole ring, an imidazole ring, a thiazole ring, an oxazole ring, a thiadiazole ring, an oxadiazole ring, a triazole ring, a tetrazole ring, a pyridine ring, a pyrimidine ring, a pyrazine ring, a triazine ring, a benzoxazole ring, a benzothiazole ring, a benzimidazole ring, a benzopyrazole ring, a quinoline ring, an isoquinoline ring, and the like are exemplified, and, among these, a pyridine ring, a benzoxazole ring, a benzothiazole ring, and a quinoline ring are more preferred, a pyridine ring, a benzoxazole ring, and a benzothiazole ring are still more preferred, and a pyridine ring is particularly preferred.

In a case in which there is a plurality of X's, the plurality of X's is identical to or different from each other.

$R^4$ represents an alkyl group, an aryl group, an alkoxy group, a carbonyl group-containing group, a sulfonyl group-containing group, or a halogen atom. Meanwhile, $R^4$ may be a group obtained by combining these groups.

Preferred forms of the alkyl group, the aryl group, the alkoxy group, the carbonyl group-containing group, the sulfonyl group-containing group, or the halogen atom that are represented by $R^4$ are identical to the preferred forms of the alkyl group, the aryl group, the alkoxy group, the carbonyl group-containing group, the sulfonyl group-containing group, or the halogen atom as $R^1$ respectively.

q represents an integer of 0 to 3. An integer of 0 to 2 is preferred, and 0 or 1 is more preferred.

l represents an integer of 0 or more. An integer of 0 to 4 is preferred, an integer of 0 to 2 is more preferred, and 0 or 1 is particularly preferred.

As the substituent T that the respective compounds may have, the following substituents are exemplified.

The substituent is an alkyl group (preferably an alkyl group having 1 to 20 carbon atoms; for example, methyl, ethyl, isopropyl, t-butyl, pentyl, heptyl, 1-ethylpentyl, benzyl, 2-ethoxyethyl, 1-carboxymethyl, or the like), an alkenyl group (preferably an alkenyl group having 2 to 20 carbon atoms, for example, vinyl, allyl, oleyl, or the like), an alkynyl group (preferably an alkynyl group having 2 to 20 carbon atoms, for example, ethynyl, butadiynyl, phenylethynyl, or the like), a cycloalkyl group (preferably a cycloalkyl group having 3 to 20 carbon atoms, for example, cyclopropyl, cyclopentyl, cyclohexyl, 4-methylcyclohexyl, or the like), an aryl group (preferably an aryl group having 6 to 26 carbon atoms, for example, phenyl, 1-naphthyl, 4-methoxyphenyl, 2-chlorophenyl, 3-methylphenyl, or the like), a heterocyclic group (preferably a heterocyclic group having 2 to 20 carbon atoms, more preferably a five- or six-membered heterocyclic group having at least one oxygen atom, sulfur atom, or nitrogen atom, for example, 2-pyridyl, 4-pyridyl, 2-imidazolyl, 2-benzoimidazolyl, 2-thiazolyl, 2-oxazolyl, or the like), an alkoxy group (preferably an alkoxy group having 1 to 20 carbon atoms, for example, methoxy, ethoxy, isopropyloxy, benzyloxy, or the like), an aryloxy group (preferably an aryloxy group having 6 to 26 carbon atoms, for example, phenoxy, 1-naphthyloxy, 3-methylphenoxy, 4-methoxyphenoxy, or the like), an alkoxycarbonyl group (preferably an alkoxycarbonyl group having 2 to 20 carbon atoms, for example, ethoxycarbonyl, 2-ethylhexyloxycarbonyl, or the like), an amino group (preferably an amino group having 0 to 20 carbon atoms, an alkylamino group and an arylamino group are included, for example, amino, N,N-dimethylamino, N,N-diethylamino, N-ethylamino, anilino, or the like), a sulfamoyl group (preferably a sulfamoyl group having 0 to 20 carbon atoms, for example, N,N-dimethylsulfamoyl, N-phenylsulfamoyl, or the like), an acyl group (preferably an acyl group having 1 to 20 carbon atoms, for example, acetyl, propionyl, butyryl, benzoyl, or the like), an acyloxy group (preferably an acyloxy group having 1 to 20 carbon atoms, for example, acetyloxy, benzoyloxy, or the like), a carbamoyl group (preferably a carbamoyl group having 1 to 20 carbon atoms, for example, N,N-dimethylcarbamoyl, N-phenylcarbamoyl, or the like), an acylamino group (preferably an acylamino group having 1 to 20 carbon atoms, for example, acetylamino, benzoylamino, or the like), a sulfonamido group (preferably a sulfonamido group having 0 to 20 carbon atoms, for example, methanesulfonamide, benzenesulfonamide, N-methylmethanesulfonamide, N-ethylbenzenesulfonamide, or the like), an alkylthio group (preferably an alkylthio group having 1 to 20 carbon atoms, for example, methylthio, ethylthio, isopropylthio, benzylthio, or the like), an arylthio group (preferably an arylthio group having 6 to 26 carbon atoms, for example, phenylthio, 1-naphthylthio, 3-methylphenylthio, 4-methoxyphenylthio, or the like), an alkyl- or arylsulfonyl group (preferably an alkyl- or arylsulfonyl group having 1 to 20 carbon atoms, for example, methylsulfonyl, ethylsulfonyl, benzenesulfonyl, or the like), a hydroxyl group, a cyano group, or a halogen atom (for example, a fluorine atom, a chlorine atom, a bromine atom, an iodine atom, or the like), more preferably an alkyl group, an alkenyl group, an aryl group, a heterocyclic group, an alkoxy group, an aryloxy group, an alkoxycarbonyl group, an amino group, an acylamino group, a hydroxyl group, or a halogen atom, and particularly preferably an alkyl group, an alkenyl group, a heterocyclic group, an alkoxy group, an alkoxycarbonyl group, an amino group, an acylamino group, or a hydroxyl group.

In addition, the respective groups exemplified as the substituent T may be further substituted with the substituent T.

When a compound, a substituent, or the like includes an alkyl group, an alkenyl group, or the like, the alkyl group, the alkenyl group, or the like may be linear or branched and may be substituted or unsubstituted. In addition, when a compound, a substituent, or the like includes an aryl group, a heterocyclic group, or the like, the aryl group, the heterocyclic group, or the like may be a single ring or a condensed ring and may be substituted or unsubstituted.

Meanwhile, a substance expressed as a compound or a complex in the present specification refers not only to the compound or the complex but also to a salt or an ion thereof. For example, in the case of expressing "including the metal complex (I)", this means that the metal complex (I) may be present in the electrolytic solution in an ion or salt form. In addition, the substance also refers to a substance obtained by changing the structure of a specific part of the substance as long as a desired effect exhibited. In addition, a substituent and a linking group that is not expressed as substituted or unsubstituted in the present specification means that the substituent and the linking group may have a random substituent therein. What has been described above also shall apply to a compound that is not expressed as substituted or unsubstituted. As a preferred substituent, the substituent T is exemplified.

Specific examples of the metal complex (I) that is used in the present invention will be shown below, but the present invention is not interpreted to be limited thereto. Meanwhile, in exemplary compounds (A-8) to (A-12) shown below, bonds between a carbon atom and a nitrogen atom intersecting each other indicate that the carbon atom and the nitrogen atom bond together through a double bond and indicate both a cis body and a trans body.

(A-1)

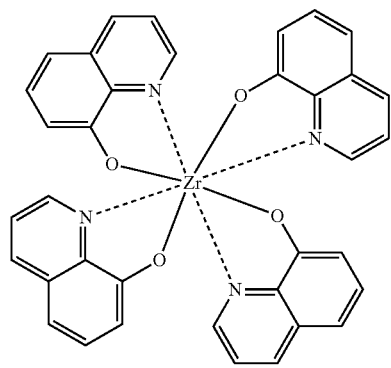

(A-2)

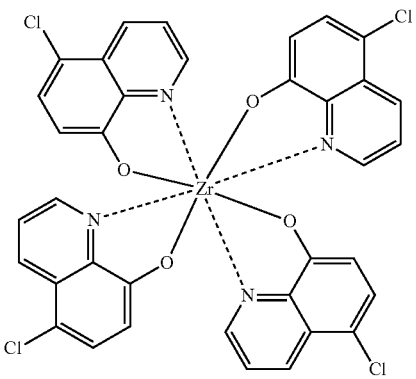

(A-3)

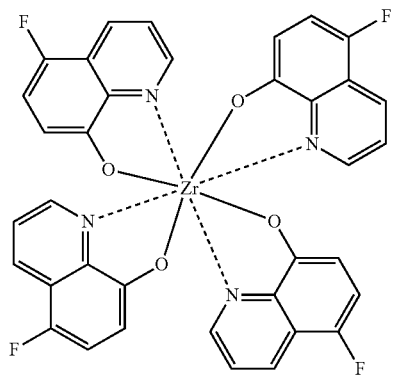

(A-4)

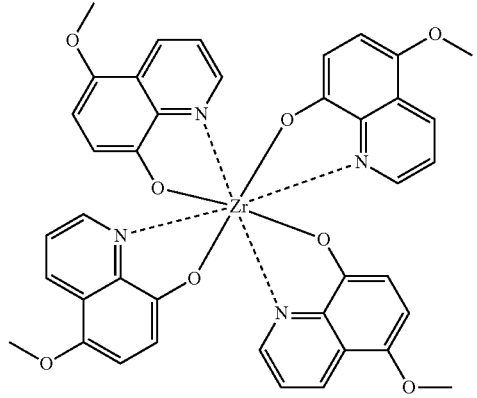

(A-5)

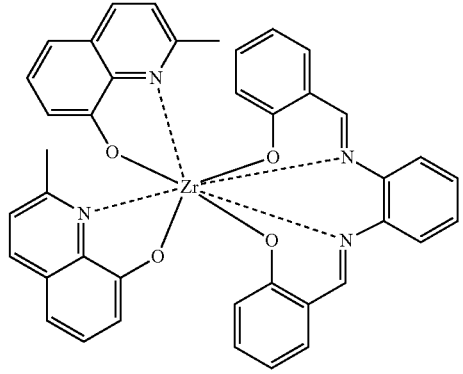

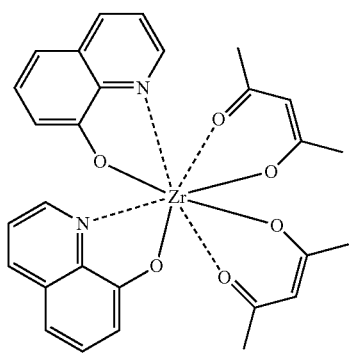
(A-6)
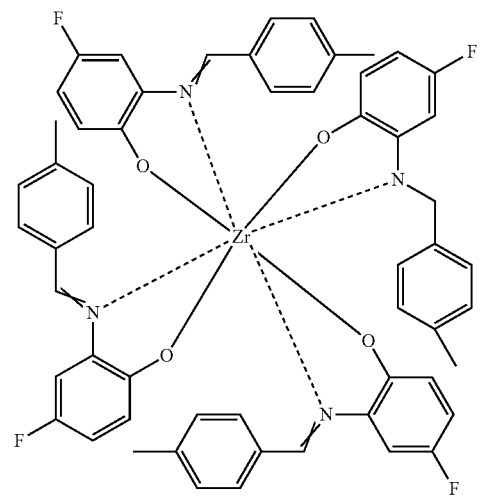
(A-9)
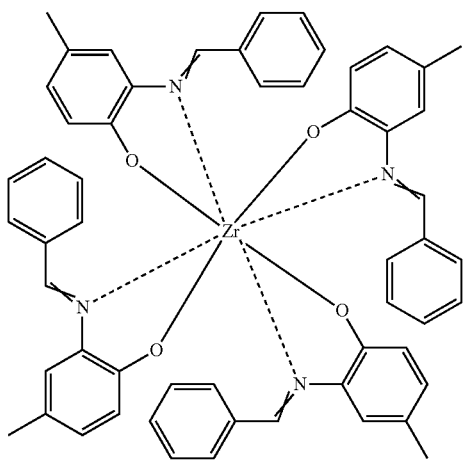
(A-7)
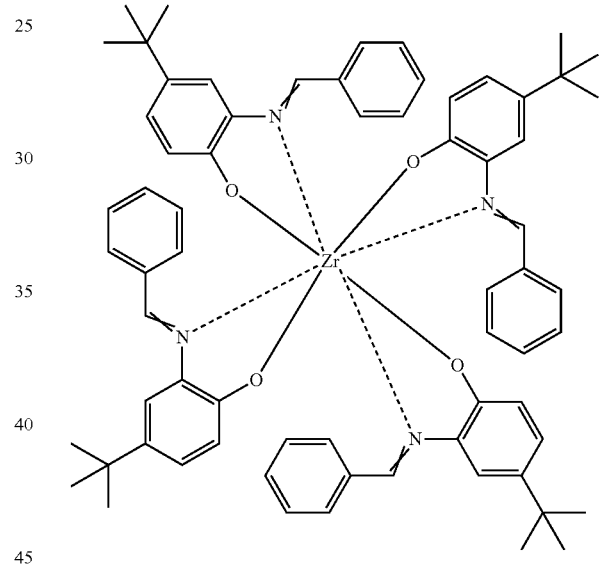
(A-10)
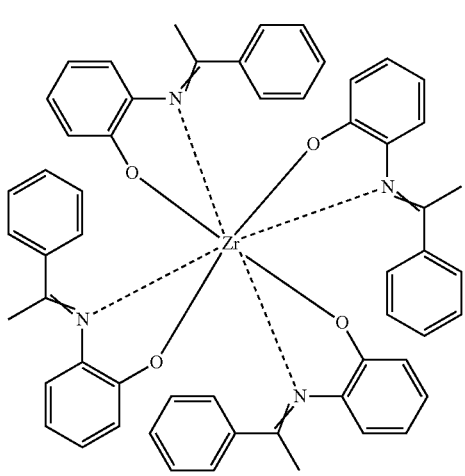
(A-8)
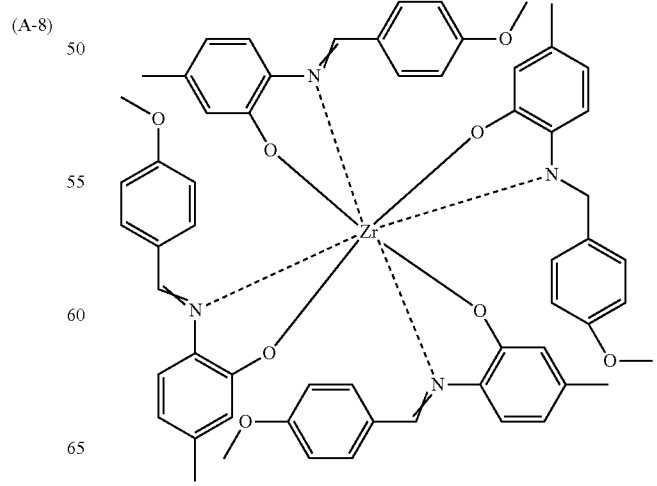
(A-11)

-continued (A-12)

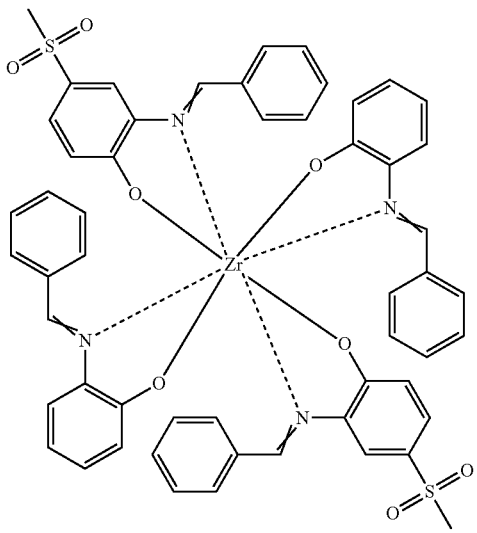

The metal complex (I) that is used in the present invention can be obtained using an ordinary method.

Here, an assumed action mechanism of the metal complex (I) that suppresses the oxidation and decomposition of components such as the organic solvent included in the electrolytic solution for a non-aqueous secondary battery in a non-aqueous secondary battery of the embodiment of the present invention will be described. Here, the present invention is not interpreted to be limited by the description of the action mechanism.

In a preferred embodiment of the present invention, it is assumed that a decomposition reaction of the metal complex (I) on the positive electrode surface takes part in the suppression of the oxidation and decomposition. Particularly, it is considered that the action becomes significant in a high-potential positive electrode. That is, it is considered that, in the case of driving a non-aqueous secondary battery at a high potential (for example, approximately 5 V), due to oxidation on the positive electrode surface, a certain reaction proceeds, and a protective film (SEI coating) including the metal complex (I) as a matrix is formed on the positive electrode surface. As a result, it is assumed that the direct contact between the positive electrode and the electrolytic solution for a non-aqueous secondary battery is effectively suppressed and the oxidation and decomposition of components such as the organic solvent included in the electrolytic solution is suppressed.

Here, in the metal complex (I) that is used in the present invention, as shown in General Formula (I), a nitrogen atom is present in an ortho position with respect to a carbon atom of a benzene ring to which an oxygen atom bonds, the oxygen atom bonds to a transition metal M, and the nitrogen atom coordinates to the transition metal M through a lone electron. Therefore, the metal complex (I) is in a state in which the decomposition potential is appropriately adjusted. As a result, it is assumed that the metal complex (I) decomposes at a high potential at which a positive electrode active material is capable of intercalating and deintercalating Li ions, and the SEI coating is more selectively formed on the surface of the positive electrode active material layer, whereby the oxidation and decomposition of the organic solvent or the like included in the electrolytic solution are more effectively suppressed.

The content of the metal complex (I) in the electrolytic solution for a non-aqueous secondary battery of the embodiment of the present invention is preferably approximately 0.05% by mass to 5% by mass, more preferably approximately 0.05% by mass to 1% by mass, and still more preferably 0.05% by mass to 0.5% by mass. In addition, with respect to 100 parts by mass of the electrolyte, the content of the metal complex (I) in the electrolytic solution for a non-aqueous secondary battery of the embodiment of the present invention is preferably 0.05 to 5 parts by mass and more preferably 0.25 to 2.5 parts by mass.

In a case in which the content of the metal complex (I) is in the above-described range, it is possible to effectively suppress (1) an increase in resistance in the non-aqueous secondary battery and (2) the oxidation of the electrolytic solution for a non-aqueous secondary battery that is included in the non-aqueous secondary battery.

(Functional Additive)

The electrolytic solution for a non-aqueous secondary battery of the embodiment of the present invention may contain at least one type of a variety of functional additives of (A) to (G). Examples of functions that are developed by these additives include the improvement of flame retardance, the improvement of cycle characteristics, and the improvement of capacity characteristics and the like. Some of the following additives can also be used as the organic solvent, but also can be used as additives with an intention of developing the above-described functions in the present invention.

<Aromatic Compound (A)>

As an aromatic compound, a biphenyl compound and an alkyl-substituted benzene compound are exemplified. The biphenyl compound has a partial structure in which two benzene rings are bonded together through a single bond, the benzene ring may have a substituent, and preferred substituents are an alkyl group having 1 to 4 carbon atoms (for example, methyl, ethyl, propyl, t-butyl, or the like) and an aryl group having 6 to 10 carbon atoms (for example, phenyl, naphthyl, or the like).

Specific examples of the biphenyl compound include biphenyl, o-terphenyl, m-terphenyl, p-terphenyl, 4-methylbiphenyl, 4-ethylbiphenyl, 4-t-butylbiphenyl, and the like.

The alkyl-substituted benzene compound is preferably a benzene compound substituted with an alkyl group having 1 to 10 carbon atoms, and specific examples thereof include cyclohexylbenzene, t-amylbenzene, t-butylbenzene, and the like.

<Halogen-Containing Compound (B)>

A halogen atom that the halogen-containing compound has is preferably a fluorine atom, a chlorine atom, or a bromine atom and more preferably a fluorine atom. The number of halogen atoms is preferably one to six and more preferably one to three. The halogen-containing compound is preferably a carbonate compound substituted with a fluorine atom, a polyether compound having a fluorine atom, or a fluorine-substituted aromatic compound.

The halogen-containing compound is preferably a halogen-substituted carbonate compound, and the halogen-substituted carbonate compound may have any of a chain shape or a cyclic shape; however, from the viewpoint of the ion conductivity, a cyclic carbonate compound having a high coordinating property of a metal ion (for example, a lithium ion) of the electrolyte salt is preferred, and a five-membered cyclic carbonate compound is particularly preferred.

Specific preferred examples of the halogen-substituted carbonate compound will be shown below. Among them, compounds of Bex1 to Bex4 are preferred, and Bex1 is particularly preferred.

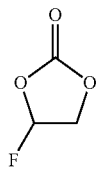
Bex1

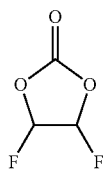
Bex2

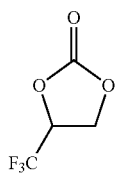
Bex3

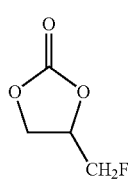
Bex4

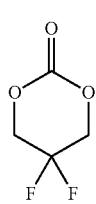
Bex5

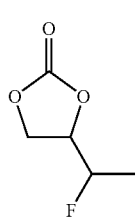
Bex6

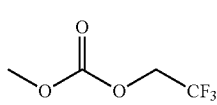
Bex7

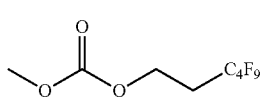
Bex8

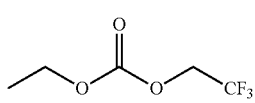
Bex9

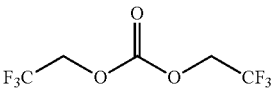
Bex10

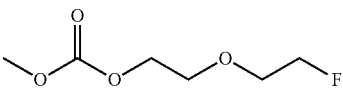
Bex11

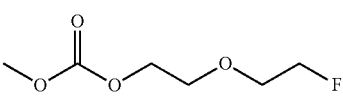
Bex12

<Polymerizable Compound (C)>

As a polymerizable compound, a compound having a carbon-carbon double bond is preferred, a carbonate compound having a double bond such as vinylene carbonate or vinyl ethylene carbonate, a compound having a group selected from an acrylate group, a methacrylate group, a cyanoacrylate group, and an αCF₃ acrylate group, and a compound having a styryl group are preferred, and a carbonate compound having a double bond and a compound having two or more polymerizable groups in the molecule are more preferred.

<Phosphorus-Containing Compound (D)>

As a phosphorus-containing compound, a phosphoric acid ester compound and a phosphazene compound are preferred. Preferred examples of the phosphoric acid ester compound include trimethyl phosphate, triethyl phosphate, triphenyl phosphate, and tribenzyl phosphate. The phosphorus-containing compound is also preferably a compound represented by Formula (D2) or (D3).

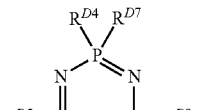

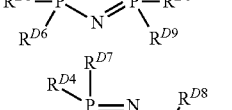

In the formulae, $R^{D4}$ to $R^{D11}$ represent a monovalent substituent. The monovalent substituent is preferably an alkyl group, an aryl group, an alkoxy group, an aryloxy group, an amino group, or a halogen atom (for example, a fluorine atom, a chlorine atom, or a bromine atom). At least one of the substituents of $R^{D4}$ to $R^{D11}$ is preferably a fluorine atom and more preferably an alkoxy group, an amino group, or a substituent made of a fluorine atom.

<Sulfur-Containing Compound (E)>

As a sulfur-containing compound, a compound having a —SO₂—, —SO₃—, or —OS(=O)O— bond is preferred, and cyclic sulfur-containing compounds such as propane sultone, propene sultone, and ethylene sulfite and sulfonic acid esters are preferred.

As the cyclic sulfur-containing compound, a compound represented by Formula (E1) or (E2) is preferred.

(E1)
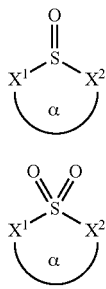

(E2)

In the formulae, $X^{E1}$ and $X^{E2}$ each independently represent —O— or —C(Ra)(Rb)—. Here, Ra and Rb each independently represent a hydrogen atom or a substituent. The substituent is preferably an alkyl group having 1 to 8 carbon atoms, a fluorine atom, or an aryl group having 6 to 12 carbon atoms. α represents an atomic group necessary to form a five- or six-membered ring. The skeleton of α may include a sulfur atom, an oxygen atom, or the like in addition to a carbon atom. α may be substituted, examples of a substituent include the substituent T, and the substituent is preferably an alkyl group, a fluorine atom, or an aryl group.

Specific examples of the compound represented by Formula (E1) or (E2) will be shown below.

Eex1
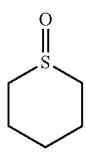

Eex2
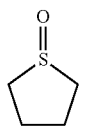

Eex3
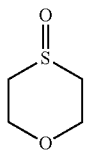

Eex4
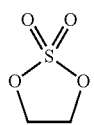

Eex5

Eex6

Eex7
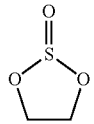

Eex8
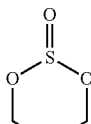

Eex9
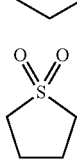

Eex10
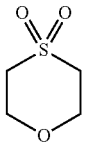

Eex11
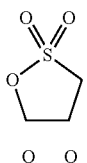

Eex12
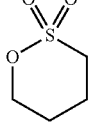

<Silicon-Containing Compound (F)>

As a silicon-containing compound, a compound represented by Formula (F1) or (F2) is preferred.

(F1)
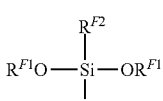

(F2)
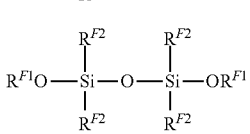

$R^{F1}$ represents an alkyl group, an alkenyl group, an acyl group, an acyloxy group, or an alkoxycarbonyl group.

$R^{F2}$ represents an alkyl group, an alkenyl group, an alkynyl group, or an alkoxy group. Meanwhile, a plurality of $R^{F1}$'s or $R^{F2}$'s in one formula may be different from or identical to each other.

<Nitrile Compound (G)>

As a nitrile compound, a compound represented by Formula (G) is preferred.

(G)
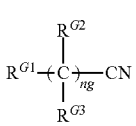

In the formula, $R^{G1}$ to $R^{G3}$ each independently represent a hydrogen atom, an alkyl group, an alkoxycarbonyl group, an aryloxycarbonyl group, a cyano group, a carbamoyl group, a sulfonyl group, or a phosphonyl group. Regarding preferred examples of the respective substituents, the examples of the above-described substituent T can be referred to, and, among them, a compound having a plurality of nitrile groups in which any one or more of $R^{G1}$ to $R^{G3}$ include a cyano group is preferred. ng represents an integer of 1 to 8.

Specific examples of the compound represented by Formula (G) include acetonitrile, propionitrile, isobutyronitrile, succinonitrile, malononitrile, glutaronitrile, adiponitrile, 2-methylglutaronitrile, hexanetricarbonitrile, propane tetracarbonitrile, and the like. Preferred are succinonitrile, malononitrile, glutaronitrile, adiponitrile, 2-methylglutaronitrile, hexanetricarbonitrile, and propane tetracarbonitrile.

The content of the functional additive is preferably 0.01 to 0.5 mol/L and more preferably 0.05 to 0.3 mol/L with respect to the entire electrolytic solution for a non-aqueous secondary battery.

The content of the functional additive is preferably 200 to 5,000 parts by mass and, from the viewpoint of the amount of SEI coating formed on the electrode surface, more preferably 500 to 2,000 parts by mass with respect to 100 parts by mass of the metal complex (I).

(Other Functional Additives)

The electrolytic solution for a non-aqueous secondary battery of the embodiment of the present invention may contain at least one of a negative electrode coating-forming agent, a flame retardant, an overcharge inhibitor, or the like. The content of each of these functional additives in the electrolytic solution is not particularly limited, but is preferably 0.001% by mass to 10% by mass with respect to the total mass of the electrolytic solution for a non-aqueous secondary battery. Due to the addition of these compounds, it is possible to effectively suppress the breakage and/or ignition of a battery during abnormality caused by overcharge or further improve the capacity retention characteristics after storage at a high temperature and the cycle characteristics.

[Method for Preparing Electrolytic Solution for Non-Aqueous Secondary Battery]

The electrolytic solution for a non-aqueous secondary battery can be prepared using an ordinary method by dissolving the respective components described above, including an example in which a lithium salt is used as the salt of a metal ion, in an organic solvent. Here, in the present invention, the expression "non-aqueous" in the electrolytic solution for a non-aqueous secondary battery means that the electrolytic solution substantially does not include water. The expression "substantially not including water" means that the electrolytic solution may include water as long as the effect of the present invention is not impaired. In this case, the content of water is preferably 200 ppm (mass-based) or less and more preferably 100 ppm or less. The lower limit value is not particularly limited, but is realistically 10 ppm or more when the inevitable mixing of water is taken into account.

The viscosity of the electrolytic solution for a non-aqueous secondary battery is not particularly limited, but is preferably 0.1 to 10 mPa·s and more preferably 0.5 to 5 mPa·s at 25° C.

In the present invention, unless particularly otherwise described, a value measured using the following measurement method is used as the viscosity of the electrolytic solution for a non-aqueous secondary battery of the embodiment of the present invention.

<Method for Measuring Viscosity>

The electrolytic solution for a non-aqueous secondary battery (1 mL) was put into a rheometer (CLS 500), and the viscosity is measured using a Steel Cone (both are trade names, manufactured by TA Instruments) having a diameter of 4 cm/2°. The sample is kept warm in advance at a measurement-start temperature until the temperature becomes constant, and then the measurement begins. The measurement temperature is set to 25° C.

[Non-Aqueous Secondary Battery]

A non-aqueous secondary battery contains a positive electrode, a negative electrode, and an electrolytic solution. One example of a preferred embodiment of the non-aqueous secondary battery will be described with reference to FIG. 1 schematically showing a mechanism of a lithium ion non-aqueous secondary battery. Here, the non-aqueous secondary battery of the embodiment of the present invention is not interpreted to be limited by the drawing and description based on the drawing.

A lithium ion non-aqueous secondary battery 10 comprises the electrolytic solution for a non-aqueous secondary battery 5, a positive electrode C capable of intercalating and deintercalating lithium ions (a positive electrode collector 1, a positive electrode active material layer 2), and a negative electrode A capable of intercalating, deintercalating, dissolving, or precipitating lithium ions (a negative electrode collector 3, a negative electrode active material layer 4). The lithium ion non-aqueous secondary battery may be constituted by including, in addition to the above-described members, a separator 9, a collection terminal (not shown), an exterior case, or the like (not shown) disposed between the positive electrode and the negative electrode in consideration of the intended use, the shape, or the like of the non-aqueous secondary battery. If necessary, a protective element may be mounted in at least any of the inside of the non-aqueous secondary battery or the outside of the battery. In the case of providing the above-described structure, the trade a and b of lithium ions occurs in the electrolytic solution for a non-aqueous secondary battery 5, charge a and discharge 13 can be carried out, and it is possible to carry out the operation or electricity storage of an operation mechanism 6 through a circuit wire 7.

Hereinafter, there will be a case in which any one or both of the positive electrode active material layer and the negative electrode active material layer are described simply as "active material layer".

(Battery Shape)

The battery shape that is applied to the non-aqueous secondary battery of the embodiment of the present invention is not particularly limited, examples thereof include a bottomed tubular shape (coin-like shape), a bottomed square shape, a thin shape, a sheet shape, a paper shape, and the like, and the battery shape may be any of the above-described shapes. In addition, the shape of the non-aqueous secondary battery of the embodiment of the present invention may be an abnormal shape such as a horseshoe shape or a comb-like shape in consideration of the form of a system and a device into which the non-aqueous secondary battery is combined. Among these, from the viewpoint of efficiently discharging heat in the non-aqueous secondary battery to the outside, a bottomed square shape having at least one surface that is relatively flat and has a large area or a square shape such as a thin shape or a bottomed tubular shape such as a coin-like shape is preferred.

(Members Constituting Battery)

The non-aqueous secondary battery of the embodiment of the present invention includes the electrolytic solution for a non-aqueous secondary battery of the embodiment of the present invention and electrode mixtures (a positive electrode mixture and a negative electrode mixture) and may be constituted by further including a separator. Hereinafter, the respective members will be described.

(Electrode Mixtures)

The electrode mixture is a member obtained by applying a dispersion (mixture) for constituting an active material layer including an active material, a conductive agent, a binding agent, a filler, or the like onto a collector (electrode base material) and shaping the dispersion and the collector to a sheet shape. In the non-aqueous secondary battery, generally, a positive electrode active material is used as an active material in the positive electrode, and a negative electrode active material is used as an active material in the negative electrode.

Next, the respective components (the active materials, the conductive agent, the binding agent, the filler, or the like) and the like in the dispersion (mixture) for constituting the active material layer will be described.

Positive Electrode Active Material

As the positive electrode active material, a transition metal oxide is preferably used, and, particularly, the transition metal oxide having a transition element $M^a$ (one or more elements from Co, Ni, Fe, Mn, Cu, and V) is preferred. In addition, the transition metal oxide may have a mixing element $M^b$ (metal other than lithium, an element of Group I (Ia) or Group II (IIa) of the periodic table, Al, Ga, In, Ge, Sn, Pb, Sb, Bi, Si, P, B, or the like) mixed therein. Examples of the above-described transition metal oxide include transition metal oxides represented by any of Formulae (MA) to (MC) and, as other transition metal oxides, $V_2O_5$, $MnO_2$, and the like. As the positive electrode active material, a particulate positive electrode active material may also be used. Specifically, a transition metal oxide capable of reversibly intercalating and deintercalating lithium ions can be used, but the transition metal oxide represented by any of Formulae (MA) to (MC) is preferably used.

As the transition metal oxide, an oxide including the above-described transition element $M^a$ and the like are preferably exemplified. At this time, the oxide and the like may have the mixing element $M^b$ (preferably Al) or the like mixed therein. The amount of the mixing element $M^b$ mixed is preferably 0 to 30 mol % of the amount of the transition metal. In addition, a transition metal oxide synthesized by mixing lithium and the transition element so that the molar ratio of Li/$M^a$ reaches 0.3 to 2.2 is more preferred.

[Transition Metal Oxide Represented by Formula (MA) (Bedded Salt-Type Structure)]

As a lithium-containing transition metal oxide, particularly, a lithium-containing transition metal oxide represented by the following formula is preferred.

$$Li_{aa}M^1O_{bb} \qquad \text{Formula (MA)}$$

In Formula (MA), $M^1$ is identical to the $M^a$, and a preferred range thereof is also identical. aa represents 0 to 1.2 and is preferably 0.1 to 1.15 and more preferably 0.6 to 1.1. bb represents 1 to 3 and is preferably 2. Some of $M^1$'s may be substituted with the mixing element $M^b$. Meanwhile, the transition metal oxide represented by Formula (MA) typically has a bedded salt-type structure.

The transition metal oxide represented by Formula (MA) is more preferably a compound represented by each of the following formulae.

$$Li_gCoQ_k \qquad \text{Formula (MA-1)}$$

$$Li_gNiO_k \qquad \text{Formula (MA-2)}$$

$$Li_gMnO_k \qquad \text{Formula (MA-3)}$$

$$Li_5Co_jNi_{1-j}O_k \qquad \text{Formula (MA-4)}$$

$$Li_gNi_jMn_{1-j}O_k \qquad \text{Formula (MA-5)}$$

$$Li_gCo_jNi_iAl_{1-j-i}O_k \qquad \text{Formula (MA-6)}$$

$$Li_gCo_jNi_iMn_{1-j-i}O_k \qquad \text{Formula (MA-7)}$$

In Formulae (MA-1) to (MA-7), g is identical to the aa, and a preferred range thereof is also identical. j represents 0.1 to 0.9. i represents 0 to 1. Here, 1−j−i reaches 0 or more. k is identical to the bb, and a preferred range thereof is also identical.

Specific examples of the transition metal oxide represented by any of Formulae (MA-1) to (MA-7) include $LiCoO_2$ (lithium cobalt oxide [LCO]), $LiNi_2O_2$ (lithium nickelate), $LiNi_{0.85}Co_{0.01}Al_{0.05}O_2$ (lithium nickel cobalt aluminum oxide [NCA]), $LiNi_{0.33}Co_{0.33}Mn_{0.33}O_2$ (lithium nickel manganese cobalt oxide [NMC]), and $LiNi_{0.5}Mn_{0.5}O_2$ (lithium manganese nickelate).

Although partially overlapped, in the case of expressing the transition metal oxide represented by Formula (MA) in a different manner, a compound represented as described below is also exemplified as a preferred example.

$$Li_gNi_xMn_yCo_zO_2 \; (x>0.2, y>0.2, z\geq 0, x+y+z=1) \qquad (i)$$

Representative Compounds:
$Li_gNi_{1-3}Mn_{1/3}Co_{1/3}O_2$
$Li_gNi_{1/2}Mn_{1/2}O_2$ $$Li_gNi_xCo_yAl_zO_2 \; (x>0.7, y>0.1, 0.1\geq z\geq 0.05, x+y+z=1) \qquad (ii)$$

Representative Compounds:
$Li_gNi_{0.8}Co_{0.15}Al_{0.05}O_2$

In addition, recently, as an active material that can be used at a high potential, a solid solution represented by Formula (MA-8) has been also preferred.

$$LiM^1O_2\text{—}Li_2MnO_3 \text{ solid solution} \qquad \text{Formula (MA-8)}$$

In Formula (MA-8), $M^1$ is identical to $M^1$ in Formula (MA).

[Transition Metal Oxide Represented by Formula (MB) (Spinel-Type Structure)]

As the lithium-containing transition metal oxide, particularly, a compound represented by Formula (MB) is also preferred.

$$Li_cM^2{}_2O_d \qquad \text{Formula (MB)}$$

In Formula (MB), $M^2$ is identical to the $M^a$, and a preferred range thereof is also identical. c represents 0 to 2 and is preferably 0.1 to 1.5 and more preferably 0.6 to 1.15. d represents 3 to 5 and is preferably 4.

The transition metal oxide represented by Formula (MB) is more preferably a compound represented by each of the following formulae.

$$Li_{mm}Mn_2O_{nn} \qquad \text{Formula (MB-1)}$$

$$Li_{mm}Mn_pAl_{2-p}O_{nn} \qquad \text{Formula (MB-2)}$$

$$Li_{mm}Mn_pNi_{2-p}O_{nn} \qquad \text{Formula (MB-3)}$$

In Formulae (MB-1) to (MB-3), mm is identical to c, and a preferred range thereof is also identical. nn is identical to d, and a preferred range thereof is also identical. p represents 0 to 2. Specific examples of the above-described transition metal oxide include $LiMn_2O_4$ and $LiMn_{1.5}Ni_{0.5}O_4$.

As a preferred example of the transition metal oxide represented by Formula (MB), a compound represented as described below is also exemplified.

| | |
|---|---|
| LiCoMnO$_4$ | Formula (αa) |
| Li$_2$FeMn$_3$O$_8$ | Formula (αb) |
| Li$_2$CuMn$_3$O$_8$ | Formula (αc) |
| Li$_2$CrMn$_3$O$_8$ | Formula (αd) |
| Li$_2$NiMn$_3$O$_8$ | Formula (αe) |

From the viewpoint of a high capacity and a high output, among the above-described compounds, the transition metal oxides including Ni are still more preferred.

[Transition Metal Oxide Represented by Formula (MC)]

As the lithium-containing transition metal oxide, a lithium-containing transition metal phosphorus oxide is also preferably used, and, particularly, a compound represented by Formula (MC) is also preferred.

$$Li_e M^3(PO_4)_f \qquad \text{Formula (MC)}$$

In Formula (MC), e represents 0 to 2 and is preferably 0.1 to 1.5 and more preferably 0.5 to 1.15. f represents 1 to 5 and is preferably 0.5 to 2.

$M^3$ represents one or more elements from V, Ti, Cr, Mn, Fe, Co, Ni, and Cu. $M^3$ may be substituted with, in addition to the mixing element $M^b$, other metal such as Ti, Cr, Zn, Zr, or Nb. Specific examples thereof include olivine-type iron phosphate salts such as LiFePO$_4$ and Li$_3$Fe$_2$(PO$_4$)$_3$, iron pyrophosphates such as LiFeP$_2$O$_7$, cobalt phosphate compounds such as LiCoPO$_4$, and monoclinic nasicon-type vanadium phosphate salt such as Li$_3$V$_2$(PO$_4$)$_3$ (lithium vanadium phosphate).

Meanwhile, the aa, c, g, mm, and e values indicating the composition of Li are values that change by charge and discharge and are, typically, evaluated with a value in a stable state in a case in which the transition metal oxide contains Li. Meanwhile, in Formulae (αa) to (αe), the composition of Li is indicated by a specific value, but this value also, similarly, changes by the operation of the battery.

As the positive electrode active material, among these, spinel-type lithium nickel manganate, olivine-type cobalt phosphate, or the solid solution represented by Formula (MA-8) is particularly preferred, and specific examples thereof include compounds described below.

LiNi$_{0.5}$Mn$_{1.5}$O$_4$
LiCoPO$_4$
Li$_2$MnO$_3$—LiNi$_{0.5}$Mn$_{0.5}$O$_2$ solid solution These compounds can be used at a high potential and are thus capable of increasing the battery capacity or further increasing the capacity retention even in the case of being used at a high potential, which is particularly preferred.

The positive electrode active material that is used in the non-aqueous secondary battery of the embodiment of the present invention is preferably a positive electrode active material having a charge region in which an organic metal compound can be oxidized. Specifically, a material the ordinary use of which can be maintained at a positive electrode potential (Li/Li$^+$-based) of 3.5 V or higher is preferably used. This positive electrode potential is more preferably 3.8 V or higher, still more preferably 3.9 V or higher, and particularly preferably 4.2 V or higher. This positive electrode potential is, particularly, preferably 4.5 V or higher. The upper limit is not particularly limited. However, the upper limit is realistically 5.2 V or lower. In the case of setting the positive electrode potential in the above-described range, it is possible to improve the cycle characteristics and the high-rate discharge characteristics.

Here, the expression "the ordinary use can be maintained" means that there is no case in which an electrode material deteriorates and becomes unusable even in the case of being charged at the voltage, and this potential is also referred to as the ordinary use-possible potential.

The positive electrode potential (Li/Li$^+$-based) during charge and discharge is expressed by the following expression.

(Positive electrode potential)=(negative electrode potential)+(battery voltage)

In a case in which lithium titanate is used as a negative electrode, the negative electrode potential is set to 1.55 V. In a case in which graphite is used as the negative electrode, the negative electrode potential is set to 0.1 V. The battery voltage is observed during charge, and the positive electrode potential is computed.

The electrolytic solution for a non-aqueous secondary battery of the embodiment of the present invention is particularly preferably used in combination with a high-potential positive electrode. The use of a high-potential positive electrode, generally, tends to significantly oxidize and deteriorate an electrolytic solution in a non-aqueous secondary battery and degrade the cycle characteristics. However, but the electrolytic solution for a non-aqueous secondary battery of the embodiment of the present invention is capable of suppressing the degradation and maintaining favorable performance.

Therefore, the electrolytic solution for a non-aqueous secondary battery of the embodiment of the present invention can be preferably used in the use of high-potential driving. For example, the electrolytic solution for a non-aqueous secondary battery can be used in a non-aqueous secondary battery having a driving potential of 4.6 V or higher. The upper limit is not particularly limited, but the upper limit of a realistic driving potential is 5.2 V or lower.

Here, the driving potential refers to the upper limit of the set potential during charging.

In the non-aqueous secondary battery of the embodiment of the present invention, preferably, a lithium ion non-aqueous secondary battery, the average particle size of the positive electrode active material being used is not particularly limited, but is preferably 0.1 μm to 50 μm. The specific surface area is not particularly limited, but is preferably 0.01 m$^2$/g to 50 m$^2$/g in terms of a BET method. In addition, the pH of a supernatant at the time of dissolving the positive electrode active material (5 g) in distilled water (100 ml) is preferably 7 or more and 12 or less.

In order to provide a predetermined particle size to the positive electrode active material, an ordinary crusher or classifier is used. For example, a mortar, a ball mill, an oscillatory ball mill, an oscillatory mill, a satellite ball mill, a planetary ball mill, a swirling airflow-type jet mill, a sieve, or the like is used. A positive electrode active material obtained using a firing method may be used after being washed with water, an acidic aqueous solution, an alkaline aqueous solution, or an organic solvent.

The content of the positive electrode active material is not particularly limited, but is preferably 60% to 98% by mass and more preferably 70% to 95% by mass with respect to 100% by mass of the solid component in the dispersion (mixture) for constituting the positive electrode active material layer.

Negative Electrode Active Material

The negative electrode active material is not particularly limited as long as the negative electrode active material is capable of reversibly intercalating and deintercalating lithium ions, and examples thereof include carbonaceous materials, metal oxides such as tin oxide and silicon oxide, metal complex oxides, a lithium single body, lithium alloys such as lithium aluminum alloys, metals capable of forming an alloy with lithium such as Sn and Si, and the like.

The negative electrode active material may be used singly or two or more negative electrode active materials may be jointly used in a random combination and ratio. Among these, carbonaceous materials or lithium complex oxides are preferably used.

In addition, the metal complex oxide is not particularly limited as long as the metal complex oxide is capable of absorbing and emitting lithium, but preferably contains titanium and/or lithium as constituent components from the viewpoint of high-current density charge and discharge characteristics.

The carbonaceous material that is used as the negative electrode active material is a material substantially made of carbon. Here, the expression "material substantially made of carbon" means that the material may include other atoms as long as the effect of the present invention is not impaired, and the content of the other atoms is preferably 0.1 mol % (based on the substance amount) or less and more preferably 0.01 mol % or less. The lower limit value is not particularly limited, but is realistically 0.0001 mol % or more. Examples of the material made of a carbon atom include petroleum pitch, natural graphite, artificial graphite such as highly oriented pyrolytic graphite, and carbonaceous materials obtained by firing a variety of synthetic resins such as polyacrylonitrile (PAN)-based resins and furfuryl alcohol resins. Furthermore, examples thereof also include a variety of carbon fibers such as PAN-based carbon fibers, cellulose-based carbon fibers, pitch-based carbon fibers, vapor-grown carbon fibers, dehydrated polyvinyl alcohol (PVA)-based carbon fibers, lignin carbon fibers, glassy carbon fibers, and active carbon fibers, mesophase microspheres, graphite whisker, flat graphite, and the like.

The non-aqueous secondary battery needs to include at least one of the metal oxides or the metal complex oxides that are used as the negative electrode active material. As the metal oxides and the metal complex oxides, particularly, amorphous oxides are preferred, and furthermore, chalcogenides that are reaction products between a metal element and an element belonging to Group XVI of the periodic table are also preferably used. The amorphous oxides mentioned herein refer to oxides having a broad scattering band having a peak of a 2θ value in a range of 20° to 40° in an X-ray diffraction method in which CuKα rays are used and may have crystalline diffraction lines. The highest intensity in the crystalline diffraction line appearing at the 2θ value of 40° or more and 70° or less is preferably 100 times or less and more preferably five times or less of the diffraction line intensity at the peak of the broad scattering line appearing at the 2θ value of 20° or more and 40° or less and particularly preferably does not have any crystalline diffraction lines.

In a compound group made up of the amorphous oxides and the chalcogenides, amorphous oxides of semimetal elements and chalcogenides are more preferred, and elements belonging to Groups XIII (IIIB) to XV (VB) of the periodic table, oxides made of one element or a combination of two or more elements of Al, Ga, Si, Sn, Ge, Pb, Sb, and Bi, and chalcogenides are particularly preferred. Specific examples of preferred amorphous oxides and chalcogenides include $Ga_2O_3$, $SiO$, $GeO$, $SnO$, $SnO_2$, $PbO$, $PbO_2$, $Pb_2O_3$, $Pb_2O_4$, $Pb_3O_4$, $Sb_2O_3$, $Sb_2O_4$, $Sb_2O_5$, $Bi_2O_3$, $Bi_2O_4$, $SnSiO_3$, $GeS$, $SnS$, $SnS_2$, $PbS$, $PbS_2$, $Sb_2S_3$, $Sb_2S_5$, $SnSiS_3$, and the like. In addition, these amorphous oxides may be a complex oxide with lithium oxide (for example, $Li_2SnO_2$).

In the non-aqueous secondary battery of the embodiment of the present invention, the average particle size of the negative electrode active material being used is preferably 0.1 μm to 60 μm. In order to provide a predetermined particle size, an ordinary crusher or classifier is used. For example, a mortar, a ball mill, a sand mill, an oscillatory ball mill, a satellite ball mill, a planetary ball mill, a swirling airflow-type jet mill, a sieve, or the like is preferably used. During crushing, it is also possible to carry out wet-type crushing in which water or an organic solvent such as methanol is caused to coexist as necessary. In order to provide a desired particle diameter, classification is preferably carried out. The classification method is not particularly limited, and it is possible to use a sieve, a wind powder classifier, or the like depending on the necessity. Both of dry-type classification and wet-type classification can be carried out.

The chemical formula of a compound obtained using the above-described firing method can be computed by inductively coupled plasma (ICP) emission spectroscopy as a measurement method or from the mass difference of powder before and after firing as a convenient method.

As a negative electrode active material that can be jointly used with an amorphous oxide negative electrode active material mainly containing Sn, Si, and/or Ge, carbonaceous materials capable of absorbing and emitting lithium ions or metallic lithium, lithium, lithium alloys, and metals capable of forming an alloy with lithium are preferably exemplified.

In the non-aqueous secondary battery of the embodiment of the present invention, lithium titanate, more specifically, an oxide ($Li[Li_{1/3}Ti_{5/3}]O_4$) formed by compositing lithium and titanium is also preferably used as an active material of the negative electrode.

The content of the negative electrode active material blended into the dispersion (mixture) for constituting the negative electrode active material layer is not particularly limited, but is preferably 60% to 98% by mass and more preferably 70% to 95% by mass with respect to 100% by mass of the solid component.

Conductive Agent

In the non-aqueous secondary battery of the embodiment of the present invention, any conductive agent may be used as long as the conductive agent is an electron conductive material, and an ordinary conductive agent can be randomly used. Generally, it is possible to add one or a mixture of conductive materials such as natural graphite (scaly graphite, scale-like graphite, earthy graphite, or the like), artificial graphite, carbon black, acetylene black, Ketjen black, carbon fibers, metal powder (copper, nickel, aluminum, silver, or the like), metal fibers, or polyphenylene derivatives (described in JP1984-020971A (JP-S59-020971A)). Among these, the joint use of graphite and acetylene black is particularly preferred. The content of the conductive agent is preferably 0.1% to 50% by mass and more preferably 0.5% to 30% by mass with respect to 100% by mass of the solid component in the dispersion (mixture) for constituting the active material layer. In the case of carbon black or natural graphite, the amount thereof is particularly preferably 0.5% to 15% by mass in the dispersion.

Binding Agent

As the binding agent, polysaccharides, thermoplastic resins, polymers having rubber elasticity, and the like are exemplified, and, among these, for example, an emulsion (latex) or a dispersion of starch, carboxymethyl cellulose, cellulose, diacetyl cellulose, methyl cellulose, hydroxyethyl cellulose, hydroxypropyl cellulose, sodium alginate, polyacrylic acid, sodium polyacrylate, polyvinyl phenol, polyvinyl methyl ether, polyvinyl alcohol, polyvinyl pyrrolidone, polyacrylonitrile, polyacrylamide, polyhydroxy (meth)acrylate, a water-soluble polymer such as a styrene-maleic acid copolymer, polyvinyl chloride, polytetrafluoroethylene, polyvinylidene fluoride, a tetrafluoroethylene-hexafluoropropylene copolymer, a vinylidene fluoride-tetrafluoroethylene-hexafluoropropylene copolymer, polyethylene, polypropylene, ethylene-propylene-diene terpolymer (EPDM), sulfonated EPDM, a polyvinyl acetal resin, methyl methacrylate, a (meth)acrylic acid ester copolymer containing a (meth)acrylic acid ester such as 2-ethylhexyl acrylate, a (meth)acrylic acid ester-acrylonitrile copolymer, a polyvinyl ester copolymer containing a vinyl ester such as vinyl acetate, a styrene-butadiene copolymer, an acrylonitrile-butadiene copolymer, polybutadiene, neoprene rubber, fluorine rubber, polyethylene oxide, a polyester polyurethane resin, a polyether polyurethane resin, a polycarbonate polyurethane resin, a polyester resin, a phenyl resin, an epoxy resin, or the like is preferred, and a polyacrylic acid ester-based latex, carboxymethyl cellulose, polytetrafluoroethylene, and polyvinylidene fluoride are more preferred.

The binding agent can be used singly or two or more binding agents can be used in a mixture form. The content of the binding agent is preferably 1% to 30% by mass and more preferably 2% to 10% by mass with respect to 100% by mass of the solid component in the dispersion (mixture) for constituting the active material layer. In the case of setting the amount in the above-described range, it is possible to more appropriately maintain the holding force and agglomeration force of the respective components in the dispersion.

Filler

A material that forms the filler needs to be a fibrous material, and, generally, polypropylene, an olefin-based polymer such as polyethylene, glass, or a fibrous filler made of a material such as carbon is used. The content of the filler is not particularly limited, but is preferably 0% to 30% by mass with respect to 100% by mass of the solid component in the dispersion (mixture) for constituting the active material layer.

Collector

As collectors for the positive electrode and the negative electrode, an electron conductor that is used as an ordinary collector is used.

The collector for the positive electrode is preferably aluminum, stainless steel, nickel, titanium, or, additionally, a collector obtained by treating the surface of aluminum or stainless steel with carbon, nickel, titanium, or silver, and, among these, aluminum or an aluminum alloy is more preferred.

The collector for the negative electrode is preferably aluminum, copper, stainless steel, nickel, or titanium and more preferably aluminum, copper, or a copper alloy.

Regarding the shape of the collector, generally, a collector having a film sheet-like shape is used, and it is also possible to use a net-shaped collector, a punched collector, a compact of a lathe body, a porous body, a foaming body, or a fiber group, and the like. The thickness of the above-described collector is not particularly limited, but is preferably 1 µm to 500 µm. In addition, the surface of the collector is preferably provided with protrusions and recesses by means of a surface treatment.

(Separator)

A separator that can be used in the non-aqueous secondary battery of the embodiment of the present invention is not particularly limited as long as the separator is a material having a mechanical strength that electronically insulates the positive electrode and the negative electrode, an ion-transmitting property, and the resistance to the oxidation and the resistance to reduction of a contact surface between the positive electrode and the negative electrode. As the above-described material of the separator, a porous polymer material, an inorganic material, an organic/inorganic hybrid material, a glass fiber, or the like is used. In order to ensure the safety, the separator preferably has a shut-down function, that is, a function of closing voids at 80° C. or higher to increase the resistance and blocking the current, and the closing temperature is preferably 90° C. or higher and 180° C. or lower.

The shape of holes in the separator is generally a round shape or an elliptical shape, and the size is preferably 0.05 µm to 30 µm and more preferably 0.1 µm to 20 µm. Furthermore, the shape of the holes may be a rod shape or an irregular shape as in a case in which the separator is produced using a stretching method or a phase separation method. The ratio of these holes, that is, the porosity is preferably 20% to 90% and more preferably 35% to 80%.

A separator obtained from a porous polymer material may be a separator for which a single material such as cellulose non-woven fabric, polyethylene, or polypropylene is used or a separator for which two or more complexed materials are used. A separator obtained by laminating two or more fine-porous films having different hole diameters, porosities, hole closing temperatures, and/or the like is preferred. The thickness is preferably 5 to 30 µm.

As the inorganic material, oxides such as alumina and silicon dioxide, nitrides such as aluminum nitride and silicon nitride, and sulfates such as barium sulfate and calcium sulfate are used. An inorganic material having a particle shape or a fiber shape is used. As the form of a separator obtained from the inorganic material, a thin film shape of a non-woven fabric, a woven fabric, a fine-porous film, or the like is exemplified. As a separator having a thin film shape, a separator having a hole diameter of 0.01 µm to 1 µm and a thickness of 5 µm to 50 µm is preferably used. In addition to the above-described independent thin film shape, a separator obtained by forming a complex porous layer containing the particles of the above-described inorganic substance on the surface layer of the positive electrode and/or the negative electrode using a resin binding agent can be used. For example, it is possible to form porous layers of alumina particles having a 90% particle diameter of less than 1 µm on both surfaces of the positive electrode using a fluorine resin binding agent, thereby forming a separator.

(Production of Non-Aqueous Secondary Battery)

The shape of the non-aqueous secondary battery of the embodiment of the present invention can be applied to any form of a bottomed tubular shape, a sheet shape, a bottomed square shape, and the like. The dispersion including the positive electrode active material or the negative electrode active material is mainly used by being applied (coated), dried, and compressed on the collector.

Figure 2:
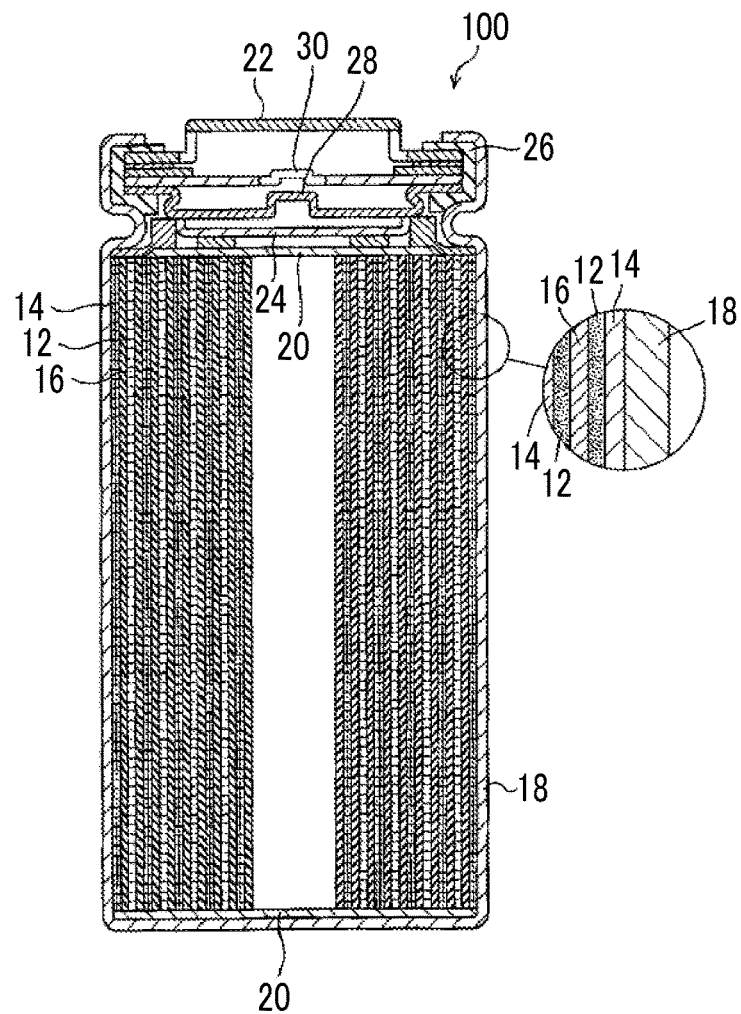
FIG. 2 is a cross-sectional view showing a specific constitution of the lithium ion non-aqueous secondary battery according to the preferred embodiment of the present invention.

Hereinafter, the constitution and the production method of a bottomed tubular-shaped lithium ion non-aqueous secondary battery 100 will be described as an example using FIG. 2. In a battery having a bottomed tubular shape, the outer surface area thereof relative to a power generation element into which the battery is loaded decreases, and thus it is preferable to provide a design in which Joule heat generated by an internal resistance during charge or discharge efficiently escapes to the outside. In addition, it is preferable to provide a design in which the loading ratio of a substance having a high thermal conduction property is increased and a temperature distribution in the battery becomes small. The bottomed tubular-shaped lithium ion non-aqueous secondary battery 100 is constituted by winding a positive electrode sheet 14 and a negative electrode sheet 16 that are laminated together through a separator 12 and storing the laminate in an exterior can 18. Additionally, a reference sign 20 represents an insulation plate, a reference sign 22 represents an opening-sealing plate, a reference sign 24 represents a positive electrode collector, a reference sign 26 represents a gasket, a reference sign 28 represents a pressure-sensitive valve body, and a reference sign 30 represents a current-blocking element. Meanwhile, in the enlarged circular drawing, the respective members are indicated using different hatchings in consideration of the visibility, but correspond to those in the overall drawing by the reference signs.

As a preferred method for producing the non-aqueous secondary battery of the embodiment of the present invention, first, the negative electrode active material and a substance obtained by dissolving the binding agent, and/or the filler, which are used as desired, in the organic solvent are mixed together, thereby preparing a slurry-form or paste-form negative electrode mixture. The obtained negative electrode mixture is uniformly and fully applied onto both surfaces of a metal core body as the collector, and then the organic solvent is removed, thereby forming a negative electrode active material layer. Furthermore, the laminate (negative electrode mixture) of the collector and the negative electrode active material layer is rolled using a roll press machine or the like so as to adjust the thickness to a predetermined thickness, thereby obtaining a negative electrode sheet (electrode sheet). A positive electrode sheet can also be obtained using the same method as for the negative electrode. At this time, a method for applying the respective agents, a method for drying applied substances, and a method for forming the positive electrode and the negative electrode may be according to ordinary methods.

(Initialization)

The non-aqueous secondary battery of the embodiment of the present invention manufactured as described above is initialized after the manufacturing or before the use, thereby forming a positive electrode SEI coating on the positive electrode surface. The initialization is not particularly limited, and, for example, the non-aqueous secondary battery can be initialized by carrying out 0.2C constant-current charge until the battery voltage reaches 4.9 V and then carrying out 1C constant-current discharge until the battery voltage reaches 2.75 V. The initialization can be carried out by repeating the above-described charge and discharge approximately three times.

In the present embodiment, a cylindrical non-aqueous secondary battery has been exemplified as an example, but the non-aqueous secondary battery of the embodiment of the present invention is not limited thereto, and, for example, a square battery may be formed by overlapping a positive electrode sheet and a negative electrode sheet produced using the above-described method through a separator so that active material layers face each other and then processing the laminate into a sheet-like battery or folding the laminate, then, inserting the laminate into a square can, electrically connecting the can and the sheets, pouring an electrolytic solution into the square can, and sealing an opening portion using an opening-sealing plate.

In all of the embodiments, it is possible to use a safety valve as the opening-sealing plate for sealing the opening portion. In addition, an opening-sealing member may comprise, in addition to the safety valve, a variety of ordinary safety elements. For example, as an overcurrent prevention element, a fuse, a bimetal, a PTC element, and the like are preferably used.

Additionally, in addition to the safety valve, as a countermeasure to an increase in the internal pressure of the battery can, it is possible to use a method in which a notch is provided in the battery can, a gasket cracking method, an opening-sealing plate cracking method, or a cutting method with a lead plate. In addition, a protective circuit into which a countermeasure to overcharging and overdischarging is incorporated may be provided to a charger or the above-described protective circuit may be independently connected to the charger.

For the battery can and the lead plate, it is possible to use a metal or alloy having electrical conductivity. For example, metal such as iron, nickel, titanium, chromium, molybdenum, copper, and aluminum or alloys thereof are preferably used.

As a method for welding a cap, the can, the sheets, and the lead plate, an ordinary method (for example, electric welding by direct current or alternating current, laser welding, or ultrasonic welding) can be used. As a sealing agent for sealing, an ordinarily-used compound or mixture such as asphalt can be used.

[Use of Non-Aqueous Secondary Battery]

The non-aqueous secondary battery of the embodiment of the present invention suppresses the deterioration of the electrolytic solution for a non-aqueous secondary battery even in the case of being driven at a high potential and is thus applied to a variety of uses. Particularly, the non-aqueous secondary battery is preferably applied to applications for which high-potential driving is demanded. For electric vehicles and the like, a use in which a high-capacity secondary battery is mounted and charged every day at home is assumed. In addition, the battery is driven with a high output, and thus a high battery voltage is required, and it becomes important to increase the battery voltage per battery in order to decrease the number of batteries. According to the present invention, it is possible to preferably deal with the above-described use form and exhibit the excellent effect.

Examples of other application forms include, in a case in which the non-aqueous secondary battery is mounted in an electronic device, notebook computers, pen-based input personal computers, mobile personal computers, e-book players, mobile phones, cordless phone handsets, pagers, handy terminals, portable faxes, mobile copiers, portable printers, headphone stereos, video movies, liquid crystal televisions, handy cleaners, portable CDs, mini discs, electric shavers, transceivers, electronic notebooks, calculators, portable tape recorders, radios, backup power supplies, memory cards, and the like. Additionally, examples of consumer uses include electric vehicles, motors, lighting equipment, toys, game devices, road conditioners, watches, strobes, cameras, medical devices (pacemakers, hearing aids, shoulder massage devices, and the like), and the like. In addition, the non-aqueous secondary battery can also be combined with a solar battery.

A metal ion that is used to transport charges in the non-aqueous secondary battery of the embodiment of the present invention is not particularly limited, but metal ions belonging to Group I or II of the periodic table are preferably used. Among them, a lithium ion, a sodium ion, a magnesium ion, and a calcium ion are preferably used, and a lithium ion is more preferably used. Regarding the general technical matters of a secondary battery for which a lithium ion is used, a number of documents and publications including the patent documents described at the front serve as references. Additionally, regarding a secondary battery for which a sodium ion is used, it is possible to refer to Journal of Electrochemical Society; Electrochemical Science and Technology, USA, 1980, Vol. 127, pp. 2,097 to 2,099 and the like. Regarding a secondary battery in which a magnesium ion is used, it is possible to refer to Nature 407, pp. 724 to 727 (2000) and the like. Regarding a secondary battery in which a calcium ion is used, it is possible to refer to J. Electrochem. Soc. Vol. 138, 3536 (1991) and the like. The electrolytic solution for a non-aqueous secondary battery of the embodiment of the present invention is broadly distributed and is thus preferably applied to a lithium ion non-aqueous secondary battery, but also exhibits a desired effect even in non-aqueous secondary batteries other than the lithium ion non-aqueous secondary battery, and thus the electrolytic solution is not interpreted to be limited thereto.

EXAMPLES

Hereinafter, examples of the present invention will be described, but the present invention is not limited by these examples by any means. Meanwhile, room temperature refers to 25° C.

Example 1

Synthesis Examples of Metal Complex (1) Synthesis of Exemplary Compound A-1

The above-described exemplary compound A-1 was synthesized in the following order.

Figure 4:
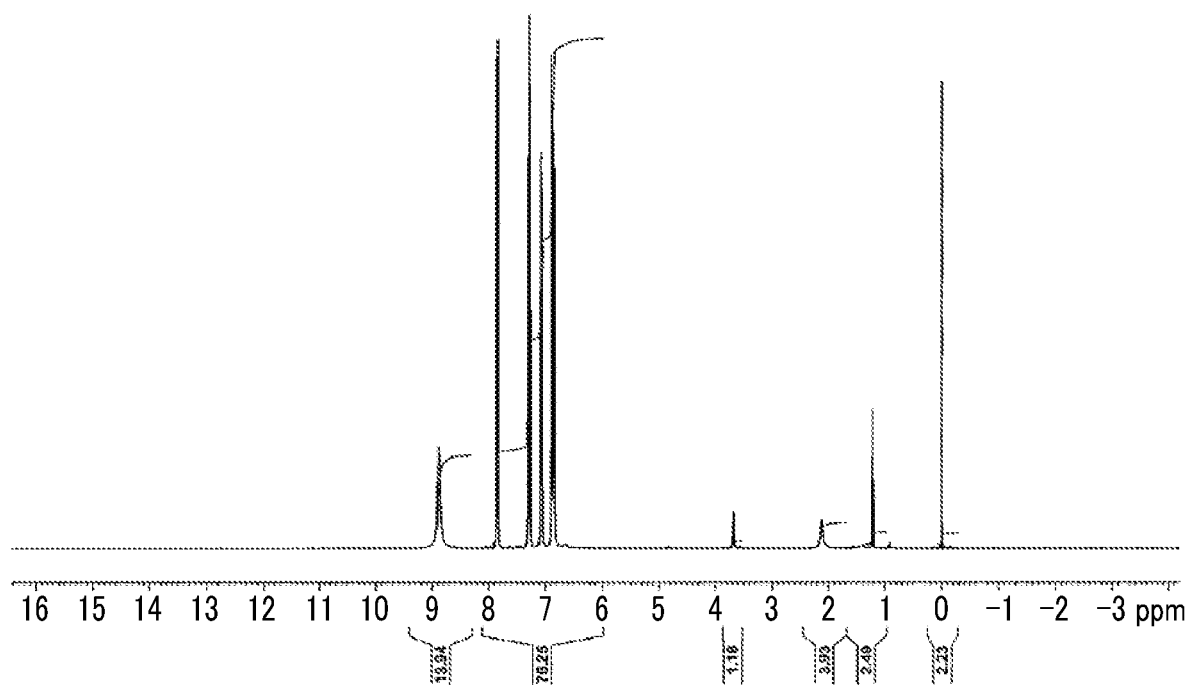
FIG. 4 is a $^1$H-NMR chart of an exemplary compound A-1 synthesized in an example.

Ethanol (100 ml) was added to zirconium tetrapropoxide (10 mmol) and 8-quinolinol (42 mmol) and stirred in a nitrogen atmosphere at a reflux temperature (80° C.) for two hours. After that, a reaction liquid was cooled to room temperature, then, filtered, washed by applying ethanol thereto, and then dried at reduced pressure, thereby obtaining a light yellow solid (yield: 92%). The synthesis of an exemplary compound A-1 was confirmed from $^1$H-NMR chart (400 MHz) shown in FIG. 4.

(2) Syntheses of Exemplary Compounds A-2 to 12 and Compounds AR-1 and AR-2

The above-described exemplary compounds A-2 to 12 and compounds AR-1 and AR-2 described below were synthesized in the same manner as the exemplary compound A-1 except for the fact that raw materials corresponding to the respective compounds were used.

The exemplary compounds A-1 to 12 are the metal complex represented by General Formula (I), and the compounds AR-1 and AR-2 are compounds for comparison.

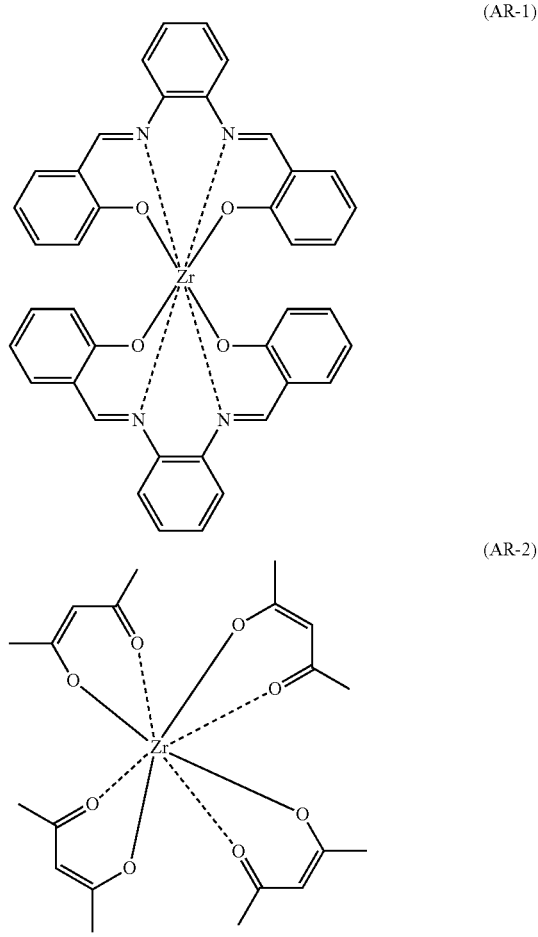

(Preparation Example of Electrolytic Solution for Non-Aqueous Secondary Battery) An ethylene carbonate/ethyl methyl carbonate (volume ratio=1:2) solution of 1 M LiPF$_6$ was added to the metal complex, adjustment was made so that the content of the metal complex reached a value shown in Table 1 below, thereby obtaining electrolytic solutions for a non-aqueous secondary battery No. 101 to 112, c102, and c103.

<Test>

For the electrolytic solutions for a non-aqueous secondary battery of No. 101 to 112 and c101 to c103, $P_{OX}$ ([%], amount of electrolytic solution oxidized) was computed using a three-pole cell.

A positive electrode that was used in the three-pole cell was produced using a mixture having the following composition and aluminum as a collector. Hereinafter, positive electrodes produced in the above-described manner will be referred to as the LNMO positive electrode.

| | |
|---|---|
| Positive electrode active material: Lithium nickel manganate (LiNi$_{0.5}$Mn$_{1.5}$O$_4$) | 85% by mass |
| Conductive agent: Carbon black | 7% by mass |
| Binder: Polyvinylidene fluoride (PVDF) | 8% by mass |

A three-pole cell was constituted using the LNMO positive electrode as an action electrode and metallic Li as a reference electrode and a counter electrode respectively, and cyclic voltammetry measurement was carried out. Specifically, for each of the electrolytic solutions for a non-aqueous secondary battery, potentials were swept under the following conditions, and a cyclic voltammogram of a total of fourth cycles was obtained.

(Cyclic Voltammetry Measurement Conditions)

Three cycles (initialization) of sweeping was carried out at

Initial potential: 3.7 V
Peak potential: 5.2 V
Finish potential: 3.7 V
Sweeping rate: 0.1 mV/s, and then
one cycle of sweeping was carried out at
Initial potential: 3.7 V
Peak potential: 5.5 V
Finish potential: 3.7 V
Sweeping rate: 0.05 mV/s.

(Computation of $P_{OX}$ [%])

Figure 3:
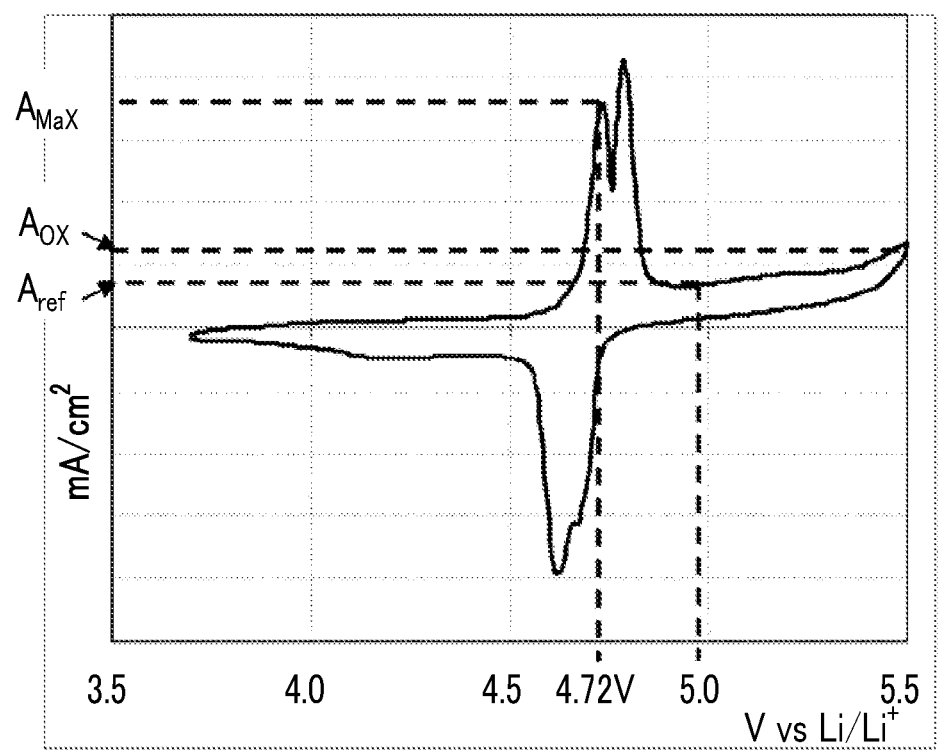
FIG. 3 is a cyclic voltammogram of an electrolytic solution for a non-aqueous secondary battery of c101 prepared in an example.

As an example, a method for computing $P_{OX}$ [%] from the cyclic voltammogram of the electrolytic solution for a non-aqueous secondary battery of c101 shown in FIG. 3 will be described. Specifically, the oxidation current amount of a peak top on a low potential side near 4.7 V was represented by $A_{Max}$, the oxidation current amount at 5.0 V was represented by $A_{ref}$, and the oxidation current amount at 5.5 V was represented by $A_{OX}$, and $P_{OX}$ [%] was computed from the following calculation expression. For the electrolytic solutions for a non-aqueous secondary battery of Nos. 101 to 112, c102, and c103, $P_{OX}$ [%] was computed in the same manner as that of the electrolytic solution for a non-aqueous secondary battery of c101. The values of $P_{OX}$ [%] are shown in Table 1 below.

$$P_{OX}[\%] = \{(A_{OX} - A_{ref})/A_{Max}\} \times 100$$

TABLE 1

| Electrolytic solution for non-aqueous secondary battery No. | Metal complex | Content of metal complex [% by mass] | $P_{OX}$ [%] |
|---|---|---|---|
| 101 | A-1 | 0.01 | 1 |
| 102 | A-2 | 0.05 | 2 |
| 103 | A-3 | 0.05 | 2 |
| 104 | A-4 | 0.008 | 1 |
| 105 | A-5 | 0.005 | 2 |
| 106 | A-6 | 0.01 | 2 |
| 107 | A-7 | 0.008 | 3 |
| 108 | A-8 | 0.01 | 4 |
| 109 | A-9 | 0.03 | 4 |
| 110 | A-10 | 0.008 | 4 |
| 111 | A-11 | 0.01 | 3 |
| 112 | A-12 | 0.01 | 4 |
| c101 | — | — | 10 |
| c102 | AR-1 | 0.01 | 8 |
| c103 | AR-2 | 0.01 | 9 |

<Notes of table>
"—" indicates that the metal complex is not contained.
"Metal complex" indicates the exemplary compounds A-1 to 12 and the compounds AR-1 and AR-2 synthesized above.

The result of using the electrolytic solution for a non-aqueous secondary battery of No. c101 shows that Pox [%] of an electrolytic solution for a non-aqueous secondary battery not containing the metal complex that is used in the present invention was great. Therefore, in the case of driving a non-aqueous secondary battery at a high potential using the above-described electrolytic solution for a non-aqueous secondary battery in the battery, it is predicted that the electrolytic solution for a non-aqueous secondary battery deteriorates and the performance of the non-aqueous secondary battery at the time of repeating charging and discharging is significantly deteriorated.

The results of using the electrolytic solutions for a non-aqueous secondary battery of Nos. c102 and c103 show that Pox [%] of an electrolytic solution for a non-aqueous secondary battery containing a compound that does not satisfy the regulation of the present invention was great. Therefore, in the case of driving a non-aqueous secondary battery at a high potential using the above-described electrolytic solution for a non-aqueous secondary battery in the battery, it is predicted that the electrolytic solution for a non-aqueous secondary battery deteriorates and the performance of the non-aqueous secondary battery at the time of repeating charging and discharging is significantly deteriorated.

Compared to the cases of using the electrolytic solutions for a non-aqueous secondary battery of Nos. c101 to c103, in the case of using the electrolytic solutions for a non-aqueous secondary battery of Nos. 101 to 112, Pox [%] was significantly low. From this result, it is found that, even in the case of being used in a non-aqueous secondary battery that is driven at a high potential, the electrolytic solution for a non-aqueous secondary battery of the embodiment of the present invention suppresses the oxidation and decomposition of organic solvents. Therefore, the non-aqueous secondary battery of the embodiment of the present invention that is produced using the electrolytic solution for a non-aqueous secondary battery of the embodiment of the present invention is, in principle, excellent in terms of the capacity retention and the storing property, and improvement in swelling can be expected.

Meanwhile, in order to use a large amount of the electrolytic solution with respect to the surface area of the active material, the test was carried out with a content of the metal complex of 0.005 to 0.05% by mass. In the non-aqueous secondary battery of the embodiment of the present invention, the amount of the electrolytic solution that is used with respect to the surface area of the active material differs. Therefore, it is assumed that the content of the metal complex is preferably approximately 0.05 to 5% by mass.

Example 2

For the electrolytic solutions for a non-aqueous secondary battery of Nos. 101 to 112 and c101 to c103, $P_{OX}$ [%] was computed in the same manner as in Example 1 except for the fact that lithium nickel manganate that was used as the positive electrode active material was changed to olivine-type lithium cobalt phosphate (LiCoPO$_4$). Values with reference to $P_{OX}$ [%] of No. c101 as 100 were obtained and evaluated using the following standards. The results are shown in Table 2 below.

—Evaluation Standards—
A: 0 or more and less than 30
B: 30 or more and less than 50
C: 50 or more and less than 70
D: 70 or more and less than 90
E: 90 or more and 100 or less

TABLE 2

| Electrolytic solution for non-aqueous secondary battery No. | Metal complex | Content of metal complex [% by mass] | $P_{OX}$ [%] |
|---|---|---|---|
| 101 | A-1 | 0.01 | A |
| 102 | A-2 | 0.05 | A |
| 103 | A-3 | 0.05 | A |
| 104 | A-4 | 0.008 | A |
| 105 | A-5 | 0.005 | A |

TABLE 2-continued

| Electrolytic solution for non-aqueous secondary battery No. | Metal complex | Content of metal complex [% by mass] | $P_{OX}$ [%] |
|---|---|---|---|
| 106 | A-6 | 0.01 | A |
| 107 | A-7 | 0.008 | B |
| 108 | A-8 | 0.01 | B |
| 109 | A-9 | 0.03 | B |
| 110 | A-10 | 0.008 | B |
| 111 | A-11 | 0.01 | B |
| 112 | A-12 | 0.01 | B |
| c101 | — | — | E |
| c102 | AR-1 | 0.01 | D |
| c103 | AR-2 | 0.01 | E |

As is clear from Table 2, the same results as in Example 1 were obtained even in the case of changing the positive electrode active material.

The present invention has been described together with the embodiment thereof; however, unless particularly otherwise specified, the present inventors did not mean to limit our invention to any detailed parts of the description, and consider that the present invention should be broadly interpreted within the concept and scope of the present invention specified in the accompanying claims.

EXPLANATION OF REFERENCES

C: positive electrode (positive electrode mixture)
1: positive electrode conductive material (collector)
2: positive electrode active material layer
A: negative electrode (negative electrode mixture)
3: negative electrode conductive material (collector)
4: negative electrode active material layer
5: electrolytic solution for non-aqueous secondary battery
6: operation mechanism
7: circuit wire
9: separator
10: lithium ion non-aqueous secondary battery
a, b: trade of lithium ions
α: travelling direction of electrons during charging
β: travelling direction of electrons during discharging
e⁻: electron
12: separator
14: positive electrode sheet
16: negative electrode sheet
18: exterior can also serving as negative electrode collector
20: insulation plate
22: opening-sealing plate
24: positive electrode collector
26: gasket
28: pressure-sensitive valve body
30: current-blocking element
100: bottomed tubular-shaped lithium ion non-aqueous secondary battery

What is claimed is:

1. An electrolytic solution for a non-aqueous secondary battery comprising:
   an electrolyte;
   an organic solvent; and
   a metal complex represented by General Formula (I),

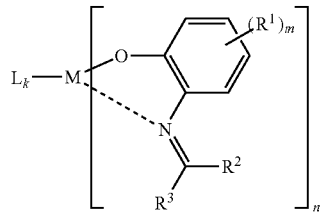

General Formula (I)

in General Formula (I), M represents a transition metal,
   k represents an integer of 0 or more, m represents an integer of 0 to 4, and n represents an integer of 1 or more, here, k+n represents a valence of M,
   $R^1$ represents an alkyl group, an aryl group, an alkoxy group, a carbonyl group-containing group, a sulfonyl group-containing group, or a halogen atom,
   $R^2$ and $R^3$ represent a hydrogen atom, an alkyl group, an aryl group, an alkoxy group, a carbonyl group-containing group, a sulfonyl group-containing group, or a halogen atom, and
   L represents a monodentate ligand.

2. The electrolytic solution for a non-aqueous secondary battery according to claim 1,
   wherein M is Ti, Zr, or Hf.

3. The electrolytic solution for a non-aqueous secondary battery according to claim 1,
   wherein a compound having a carbonate group is included as the organic solvent.

4. The electrolytic solution for a non-aqueous secondary battery according to claim 1,
   wherein a content of the metal complex represented by General Formula (I) is 0.05 to 5% by mass with respect to the total mass of the electrolytic solution.

5. A non-aqueous secondary battery comprising:
   a positive electrode;
   a negative electrode; and
   the electrolytic solution for a non-aqueous secondary battery according to claim 1.

* * * * *